(12) United States Patent
Alvarez

(10) Patent No.: US 8,083,776 B2
(45) Date of Patent: Dec. 27, 2011

(54) VERTEBRAL FIXATION DEVICE AND TOOL FOR ASSEMBLING THE DEVICE

(75) Inventor: Luis Marquez Alvarez, Reus (ES)

(73) Assignee: Traiber, S.A., Reus (Tarragona) (ES)

( * ) Notice: Subject to any disclaimer, the term of this patent is extended or adjusted under 35 U.S.C. 154(b) by 493 days.

(21) Appl. No.: 11/478,966

(22) Filed: Jun. 28, 2006

(65) Prior Publication Data

US 2007/0288004 A1 Dec. 13, 2007

(30) Foreign Application Priority Data

Jun. 5, 2006 (WO) .................. PCT/ES2006/000327

(51) Int. Cl.
*A61B 17/70* (2006.01)

(52) U.S. Cl. ......... 606/265; 606/266; 606/287; 606/305

(58) Field of Classification Search .............. 606/60, 606/246, 257, 264–274, 300–308, 319, 328, 606/250–256, 258–263, 275–279, 309–318, 606/320–327

See application file for complete search history.

(56) References Cited

U.S. PATENT DOCUMENTS

| | | | | |
|---|---|---|---|---|
| 5,672,176 | A * | 9/1997 | Biedermann et al. | 606/271 |
| 5,782,833 | A * | 7/1998 | Haider | 606/266 |
| 5,882,350 | A * | 3/1999 | Ralph et al. | 606/278 |
| 6,063,090 | A * | 5/2000 | Schlapfer | 606/270 |
| 6,287,311 | B1 * | 9/2001 | Sherman et al. | 606/78 |
| RE37,665 | E | 4/2002 | Ralph et al. | |
| 6,371,957 | B1 * | 4/2002 | Amrein et al. | 606/272 |
| 6,723,100 | B2 * | 4/2004 | Biedermann et al. | 606/308 |
| 6,835,196 | B2 | 12/2004 | Biedermann et al. | |
| 7,291,151 | B2 * | 11/2007 | Alvarez | 606/305 |
| 2002/0072752 | A1 | 6/2002 | Zucherman et al. | |
| 2002/0143341 | A1 * | 10/2002 | Biedermann et al. | 606/73 |
| 2002/0183748 | A1 * | 12/2002 | Martin et al. | 606/61 |
| 2003/0153912 | A1 * | 8/2003 | Graf | 606/61 |
| 2004/0097926 | A1 * | 5/2004 | Kim | 606/61 |
| 2004/0097933 | A1 * | 5/2004 | Lourdel et al. | 606/61 |
| 2004/0138660 | A1 * | 7/2004 | Serhan | 606/61 |
| 2004/0158247 | A1 * | 8/2004 | Sitiso et al. | 606/61 |

(Continued)

FOREIGN PATENT DOCUMENTS

EP 1210914 A1 * 6/2002

(Continued)

*Primary Examiner* — Eduardo C Robert
*Assistant Examiner* — Jerry Cumberledge
(74) *Attorney, Agent, or Firm* — Knobbe, Martens, Olson & Bear, LLP

(57) ABSTRACT

Constitutes a pedicle screw (1), a rosette (3) that fixes the pedicle screw (1) to a tulip (6), a bar that constitutes the link with other devices and a locking cap (9) associated to the closing screw (11) that is threaded on the inside of the tulip (6) and fixes the position of the bar. The locking cap (9) incorporates protuberances (12) that fit on the tulip (6), guiding the set formed by the locking cap (9) and the closing screw (11) during the positioning and threading of the closing screw (11) on the tulip (6) pressing the bar (8) against the rosette (3). The outer face of the tulip (6) and the locking cap (9) present an essentially circular configuration that is interrupted by two opposite-facing flat indentations (13, 14) that contribute to reduce the width of the device in the axial direction of the bar (8).

16 Claims, 20 Drawing Sheets

U.S. PATENT DOCUMENTS

| | | |
|---|---|---|
| 2004/0172130 A1 | 9/2004 | Nakahara et al. |
| 2004/0181224 A1* | 9/2004 | Biedermann et al. ........... 606/61 |
| 2004/0249380 A1* | 12/2004 | Glascott ........................ 606/73 |
| 2004/0260283 A1* | 12/2004 | Wu et al. ........................ 606/61 |
| 2005/0033296 A1* | 2/2005 | Bono et al. ..................... 606/61 |
| 2005/0125062 A1 | 6/2005 | Biedermann et al. |
| 2005/0131542 A1 | 6/2005 | Benzel et al. |
| 2005/0171542 A1* | 8/2005 | Biedermann et al. ........... 606/61 |
| 2005/0203516 A1* | 9/2005 | Biedermann et al. ........... 606/61 |
| 2005/0277928 A1* | 12/2005 | Boschert ........................ 606/61 |
| 2006/0200247 A1 | 9/2006 | Charrois |
| 2007/0142843 A1 | 6/2007 | Dye |
| 2008/0077153 A1 | 3/2008 | Pernsteiner et al. |

FOREIGN PATENT DOCUMENTS

| | | |
|---|---|---|
| EP | 1 210 914 B1 | 5/2005 |
| MX | 9910355 A | 4/2000 |
| WO | WO 2005/016161 A1 * | 2/2005 |

* cited by examiner

VERTEBRAL FIXATION DEVICE AND TOOL FOR ASSEMBLING THE DEVICE

OBJECT OF THE INVENTION

This invention belongs to the field of bone surgery and refers to a device that has been specially designed to immobilise two or more vertebrae in collaboration with another similar device linked to the same bar.

The object of the invention consists of developing a first vertebral fixation device with optimised configuration that allow to adjust the various elements that make it up, particularly when it is being assembled on the bone, thereby ensuring that the elements are more firmly attached and that the system is stronger, while also aiming to minimise the space occupied by the device.

A further object of the invention is the tool that is used to assemble and make the final adjustments to the elements that make up this first device, once it has been previously screwed to the bone.

A still further object of the invention is a second vertebral fixation device that consists of a lateral connector that allows correcting lateral deviations between vertebrae.

BACKGROUND TO THE INVENTION

Invention patent no. ES 2 153 331 refers to an intervertebral fixation system for spinal treatments used to immobilise two or more vertebrae through the use of bars that are attached to the bones with pedicle screws.

This system allows to install the pedicle screw on a physically separate basis from the rest of the parts that make up the device, thus allowing to fix the pedicle screw in the first instance without the bar or the means of fixing the latter to the pedicle screw preventing the viewing and therefore, the handling, of the pedicle screw while it is being fixed.

This system constitutes a pedicle screw with a spherical head intended to be inserted in the bone, a tulip enabled to receive the head of the pedicle screw, containing wide notches in order to position the bar and which constitutes a strangled opening on which the head of the pedicle screw is housed. The head of the pedicle screw is held in place by a tightening screw that moves inside the tulip and has an upper indentation on which the bar is supported.

It also includes a locking cap that moves in an axial direction along with the closing screw, which threads inside the tulip and applies pressure on the bar, thus establishing the definitive fixation and tightening of the system.

On the other hand, there is also invention patent no. WO 2005/16161, which constitutes an evolution of the system described above and also incorporates on an additional basis a supporting nut which is threaded on the outer face of the tulip and on which the bar rests, so that the tightening of the supporting nut determines the height adjustment of the bar, separating the bar from the bone.

Moreover, this invention patent incorporates an alternative system for fixation of the pedicle screw that allows to place the pedicle screw in different positions as regards the bar, unlike other systems in which only the perpendicular orientation between the bar and the pedicle screw is possible. The fixation system proposed constitutes a rosette formed by an upper promontory from which a series of flexible slats separated by slots come down, defining a housing in which the spherical head of the pedicle screw is placed. The position of the pedicle screw is fixed by a tightening screw that incides on the upper face of the promontory of the rosette in order to close the slats that press against the conical wall of the tulip, thus embracing the head of the pedicle screw.

One of the problems encountered in the use of these devices refers to the fact that because the vertebrae are very close together, it is very complicated to install the tulips on the same bar and they may even come into contact with each other.

Moreover, the installation of the set formed by the closing screw and the locking cap in the tulip is not exempt from a certain degree of complication, as there are no means to fix the position of the locking cap when the assembly commences with the screwing of the closing screw, and the locking cap prevents proper viewing of the cap-screw construct while it is being assembled in the tulip, leading to a situation where the screw may even be slanted and not thread properly in the tulip.

On the other hand, in some tulips, there is the problem that the threads on the closing screws do not thread fully onto the tulip, meaning that they could break or come loose when the device is installed on the vertebrae.

DESCRIPTION OF THE INVENTION

The vertebral fixation device proposed in this invention is intended to provide a satisfactory solution to the aforementioned problems.

Two devices shall be described, one of which will be a vertebral fixation device to immobilise the vertebrates in all kinds of cases (deviations, depth, fractures . . . ) and another vertebral fixation device that we shall refer to as a lateral connector to correct more serious lateral deviations of the vertebrates.

First of all, the main vertebral fixation device will be described, followed by the tool used to assemble this fixation device and finally, the lateral connector will be described.

The fixation device basically consists of a pedicle screw with a partially spherical head, a flexible rosette that presses on and fixes the position of the head at a particular angle, a tulip that has two lateral notches opposite each other and a cavity that holds the rosette, a bar that constitutes the connection with other devices fixed to other vertebrae and which rests against the upper head of the rosette, a locking cap with circular openings through which the bar passes, moving in an axial direction on the outer face of the tulip, and the closing screw, which is threaded on the inside of the tulip and drags the locking cap along with it in its movement and fixes the bar against one or more of the upper promontories of the rosette.

Among the improvements proposed by this invention as regards the locking cap, is the incorporation of protuberances defined on the inner face of the locking cap, placed opposite each other as a continuation of the circular openings, protuberances whose width is slightly less than that of the lateral notches of the tulip, on which it fits in order to position the construct formed by the locking cap and closing screws.

The locking cap is assembled on the closing screw according to a conventional solution in which the locking cap in question is equipped with opposite-facing fins that easily fit into the indentations on the closing screw, so that both parts are linked axially, but allow the closing screw to turn relative to the locking cap. These fins, the width of which is slightly less than that of the notches on the tulip, guide the locking cap in its movement on the tulip and prevent it from turning. However, during the initial positioning of the locking cap-closing screw construct, these fins do not fit in the notches. The internal protuberances of the locking cap that are defined in this invention solve this problem, as they first of all fit on the notches of the tulip, thus facilitating the positioning of the construct and especially, of the threaded sector of the closing screw, which penetrates on an axial basis on the thread sector of the tulip without any possible deviation, with a guided movement in which the protuberances on the locking cap move on the notches.

Another aspect of the invention refers to the absence of a complementary tightening part to fix the rosette to the head of the pedicle screw. In one possible embodiment, the bar is designed to lean directly on the promontory/ies of the rosette, so that the tightening of the closing screw causes the locking cap to press on the bar and the latter in turn on the rosette, whereas in this case, the rosette has a rough flange on the upper face of the promontory that facilitates contact between the bar and the rosette, and thus the uniform distribution of the pressure of the bar on the rosette.

In another alternative solution, the rosette incorporates a wide opening on the upper promontory which houses a bushing on which the bar exerts pressure.

In both cases, the upper promontory has a conical indentation that is prolonged inside from its perimetrical edge.

The rosette has flexible slats ending on a conical section, among which the head of the pedicle screw is housed. When the bar presses on the rosette, the pressure is transmitted to the slats that contact at their conical section with another conical section defined on the tulip, obliging the slats to close on the head of the pedicle screw, thus fixing its position.

In a usual solution, the rosette is polyaxial and configured so as to allow the head of the pedicle screw to adopt different possible orientations inside the rosette. In another possible configuration, the rosette may include on the inside a central protuberance that fits over a central hole defined on the head of the pedicle screw, in which case the pedicle screw remains perpendicular to the bar, being in this case a monoaxial rosette.

Other improvements proposed in this invention are the particular configuration of the outer face of the tulip and locking cap, for which an essentially circular general configuration has been designed, interrupted by two flat indentations opposite each other that reduce the width of both parts and therefore the space occupied by them. In the case of the tulip, the flat indentations are defined in correspondence with the side on which the notches are located, and in the case of the locking cap, the flat indentations are in correspondence with the side on which the circular openings are located.

As the circular openings and the notches define the place where the bar fits in, the incorporation of these flat indentations in correspondence with these sectors means a reduction in the width of the tulip and locking cap, and therefore, of the device, in the axial direction of the bar. This circumstance determines an increase in the distance from the device situated immediately afterwards on the same bar. Therefore, the problems that occurred before derived from the excessive proximity between the devices mounted on the same bar and applied to different vertebrae are overcome.

The absence of the tightening screw, which appears in other solutions, also allows optimising the size of the tulip, as it can be of lesser height and/or the closing screw can penetrate deeper into the tulip, making all of the threads on the lid work. This achieves better tightening conditions that prevent the threads from breaking or the cap becoming unscrewed when the device is installed on the vertebra.

Another aspect of this invention refers to the fact that the tulip has lower teeth facing each other, which penetrate very slightly into the space of the notches on the tulip in order to ensure that the bar is fixed between them. These teeth grip the bar slightly, meaning that it cannot move. The gripping of the bar reinforces the attachment of the axial movement of the bar.

The design provides that from these teeth as far as the inside threaded face of the tulip, there is a conical sector that establishes continuity and provides greater strength to the tulip, especially to reduce the tendency towards opening of the wings of the tulip, which are defined on both sides of the lateral notches, when it penetrates the locking cap.

Another aspect of the invention refers to the tool that is used to assemble the fixation device.

When the fixation device is mounted on a vertebra, the bar is positioned at a certain angle and distance from the pedicle screw of the other fixation device that is fixed to the next vertebra. During the assembly of this latter fixation device, it may occur that the bar located at the notch of the tulip may be in a position that prevents the closing screw from coming close to the threaded sector of the tulip.

The tool described hereunder has been designed to facilitate the approximation, orientation and guiding between the closing screw and the tulip in order to start and continue screwing it.

The tool is formed by a screwdriver with a handle, a base that is associated to the handle, a rod that is joined on one end to the handle and on the other end to a connector, which should preferably be hexagonal in shape, with conicity that may be fitted into the closing screw. This conicity of the connector facilitates the union between the tool and the closing screw for approximation to the tulip.

Outside the rod, there is a tube that is connected on one end to a bushing that moves from the base and on the other to a centring support that is in turn connected to a sleeve.

The sleeve has lateral notches that are destined to fit on the bar. In this situation, the closing screw, to which the connector of the screwdriver attaches, is in contact with the bar but does not actually reach the threaded sector of the tulip. The tulip that is associated to the pedicle screw and therefore to the vertebra, must move in order to allow the closing screw to enter the threaded sector of the tulip. The lever described hereunder is used for this purpose.

The lever is configured in an L-shape and is formed by a larger arm that ends in a fork whose ends are adaptable to the outer face of the base of the tulip and a smaller arm in the shape of a fork, which wings are intended for sliding along lateral indentations that are defined on the basic part of the tool.

In order to bring the tulip close to the closing screw, the lever is initially positioned, with the ends of the fork of the larger arm placed in a fixed position on the outer face of the tulip, thus becoming the points of articulation of the lever, and then the ends of the wings of the fork on the smaller arm are introduced in the lateral indentations on a bushing of the tool. In this situation, the lever forms a triangle with the rod in the tool.

Then the lever is pivoted around the articulation points, gradually introducing the wings of the fork of the smaller arm in the indentations on the bushing of the tool, thus reducing the area of the triangle described. This turn determines the progressive pushing of the ends of the fork of the larger arm of the lever on the tulip, in an axial direction and towards the rod of the tool, thus bringing the tulip closer to the closing screw until the latter manages to penetrate the threaded sector of the tulip.

In order to facilitate the extraction of the tool, the limit of the notch on the sleeve that rests on the bar means that the rod on the screwdriver may not descend any further, thus causing the automatic separation of the connector from the closing screw in the last turn of the screw.

Around the base is a reference ring initially covered by the bushing, which indicates the position of the bar in order to commence the free threading of the closing screw.

The following is a description of the auxiliary vertebral fixation device or the lateral connector that allows correcting lateral deviations between vertebrates.

This lateral connector is basically formed by an auxiliary tulip to which the bar is fixed and a rosette-carrier that is capable of turning 360° around the longitudinal axis of the auxiliary tulip, which constitutes a body in which the head of a pedicle screw is housed with the help of the rosette and the closing screw, and an arm that extends laterally and ends in a bushing that holds the auxiliary tulip around which the rosette-carrier turns.

The auxiliary tulip is open at the top and constitutes notches for the bar to pass through and an upper closing system, which may consist of the closing screw-locking cap construct described above, which presses on the bar, fixing its position on the upper face of the bushing.

The bushing on the arm is able to turn around the auxiliary tulip and fix the position of the bushing and the arm, and therefore of the rosette-carrier, is fixed by means of a lower lid that is threaded on the auxiliary tulip, meeting the bushing.

The body of the rosette-carrier has a lower cavity in which a rosette intended to hold the head of the pedicle screw is housed. The rosette has flexible slats and one or more promontories, which may be a knurled, rough or irregular surface, on which a tightening screw incides directly in order to cause the movement of the rosette, whose slats contact against the wall of the lower cavity, causing the flexion of the slats that hold the head of the pedicle screw.

In a common solution, such as the case with the main fixation device, the rosette is polyaxial and is configured in such a way that the head of the pedicle screw may adopt various possible orientations inside the rosette. In another possible configuration, the rosette may include on the inside a central protuberance that fits over a central hole defined on the head of the pedicle screw, in which case the pedicle screw remains perpendicular to the bar, whereas in this case it is a monoaxial rosette.

The aforementioned characteristics of the rosette shall also be equally valid for this lateral connector. Therefore, for example, the rosette may include a wide opening on the upper promontory, housing a bushing on which the bar exerts pressure.

The tightening screw is initially introduced through the lower cavity of the turning body and remains threaded in a threaded upper cavity containing upper limits that prevent it from coming out on top.

The body of the rosette-carrier contains holes through which it is possible to introduce a tool to grip the rosette, once the tightening screw has been unscrewed, thus facilitating the removal from the latter of the pedicle screw.

The lateral connector thus designed provides various degrees of freedom. On the one hand, the construct formed by the auxiliary tulip and the rosette-carrier on the union bar can rotate 360° and the rosette-carrier can also rotate 360° around the auxiliary tulip in the plane in which the union bar is located. It is also possible for the pedicle screw to rotate on its head inside the tulip.

DESCRIPTION OF THE DRAWINGS

In order to complement the description that is being made and with a view to helping towards a better understanding of the characteristics of the invention, according to an example of a practical embodiment of same, this description includes as an integral part of same a set of figures which on an illustrative and non-restrictive basis represent the following.

PREFERENTIAL EMBODIMENT OF THE INVENTION

Figure 1:
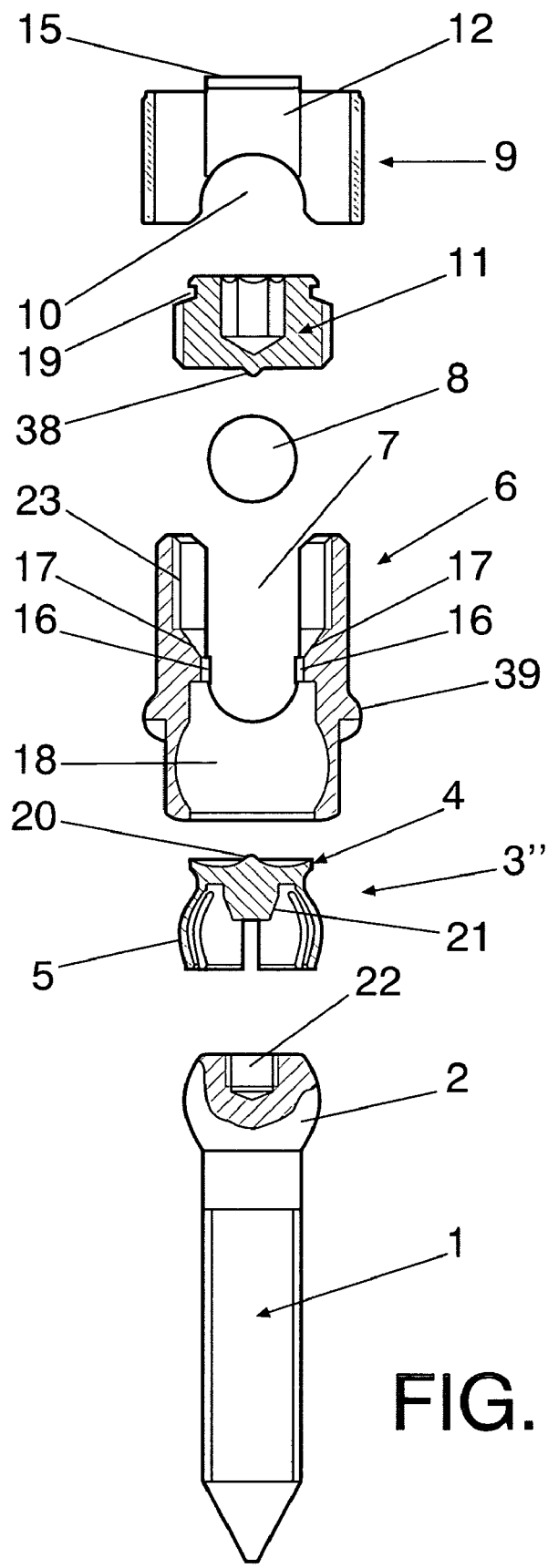
FIG. 1.—Depicts an exploded view of the sectioned elements that make up the vertebral fixation device.

According to the above figures, the following is a description of a mode of preferential embodiment for the vertebral fixation device that constitutes the object of this invention. As depicted in FIG. 1, the device includes:

a pedicle screw (1), which constitutes a head (2) whose preferred embodiment is preferably partially spherical, intended to be introduced in a vertebra, A rosette (3-3'-3") with an upper promontory (4) from which flexible slats come down (5) intended to press on the head (2), thus fixing the pedicle screw (1) and providing the system with the desired orientation, a tulip (6) with two lateral notches (7) and a lower cavity (18), partially spherical in shape, in which the rosette is housed (3-3'-3"), a bar (8), which constitutes the link with the other devices and is housed in the lateral notches (7), a locking cap (9) with circular openings (10) for the bar (8) to pass through, which moves axially on the outer face of the tulip (6), and the closing screw (11) associated to the locking cap (9) which is threaded on a threaded sector (23) inside the tulip (6) and fixes the bar (8) against the rosette (3-3'-3").

Figure 2:
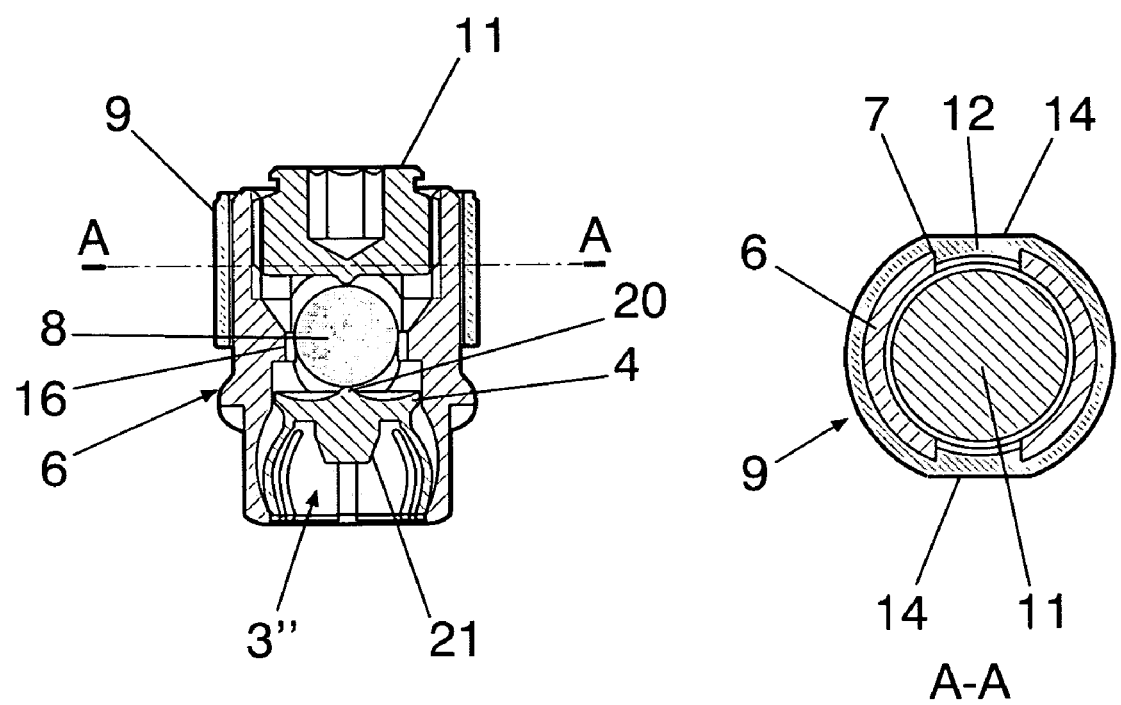
FIG. 2.—Depicts a sectioned elevation view of the fixation device with its elements in the assembly position in which the pedicle screw has not been represented, and a cut along A-A.
Figure 4:
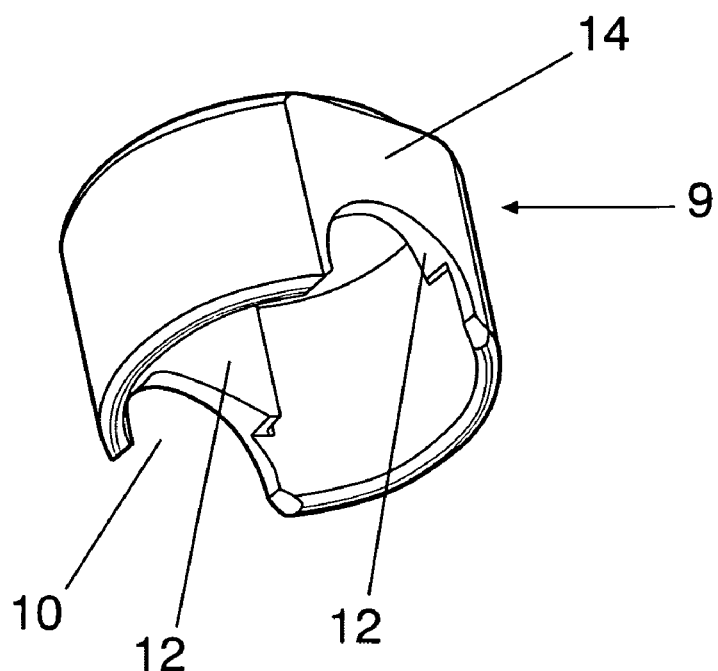
FIG. 4.—Depicts a perspective view from under the locking cap.
Figure 6:
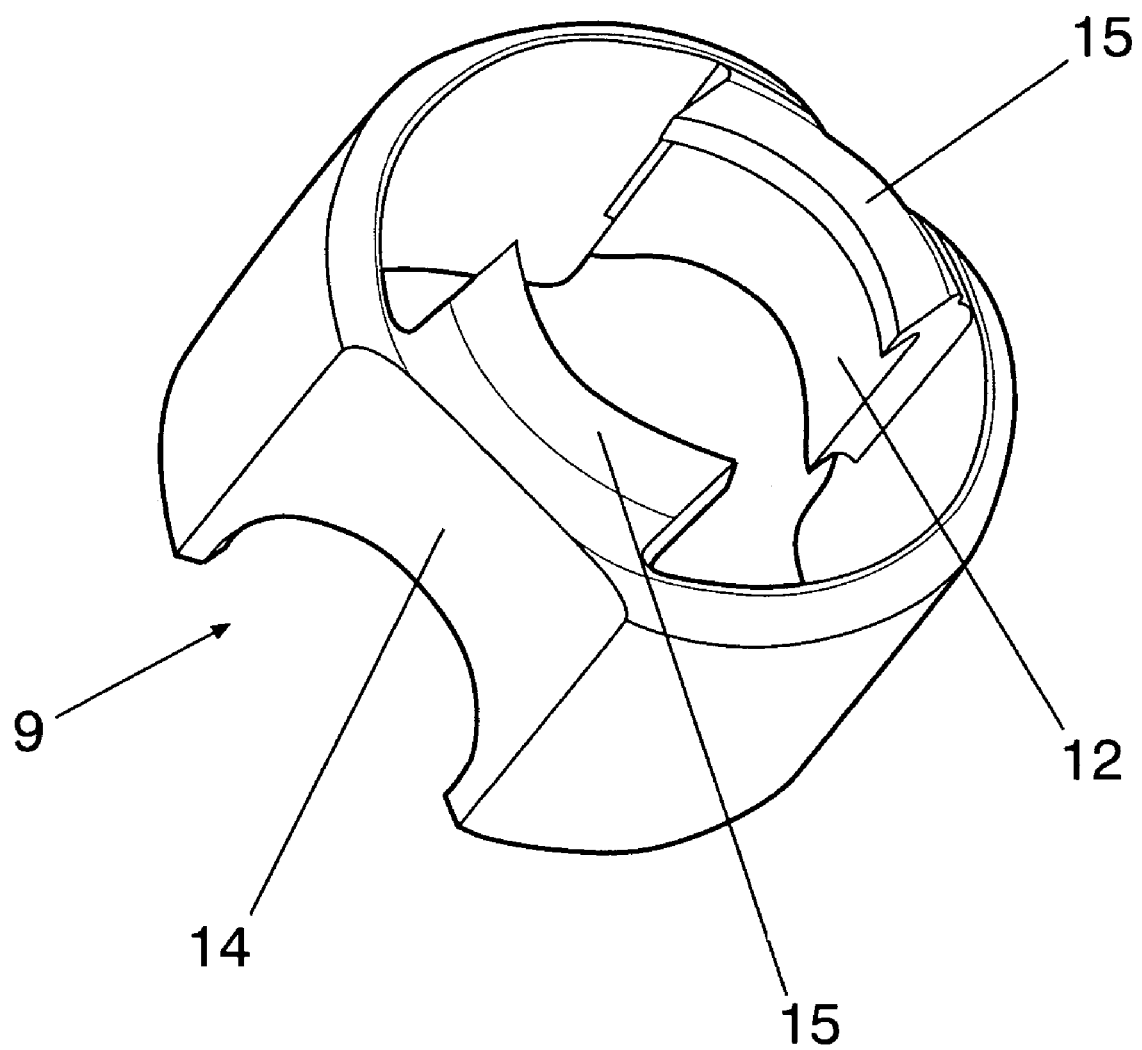
FIG. 6.—Depicts a perspective view of the locking cap from above.

As may be seen in FIG. 4 or 6, the locking cap (9) incorporates protuberances (12) that are defined on its inner face, situated opposite each other as a continuation of the circular openings (10), slightly less wide than the width of the lateral notches (7) of the tulip (6), on which it fits, as may be seen in cut A-A of FIG. 2, guiding the locking cap (9) in an axial direction and facilitating the positioning of the closing screw (11) and threading on the threaded sector (23) of the tulip (6) while also moving, pushing the bar (8) against the rosette (3-3'-3").

The internal protuberances (12) opposite each other are circular in shape, as may be seen in FIG. 6, in order to adequately house the closing screw (11), as may be seen in cut A-A of FIG. 2, guaranteeing its alignment with the tulip (6) at the moment threading commences.

Figure 3:
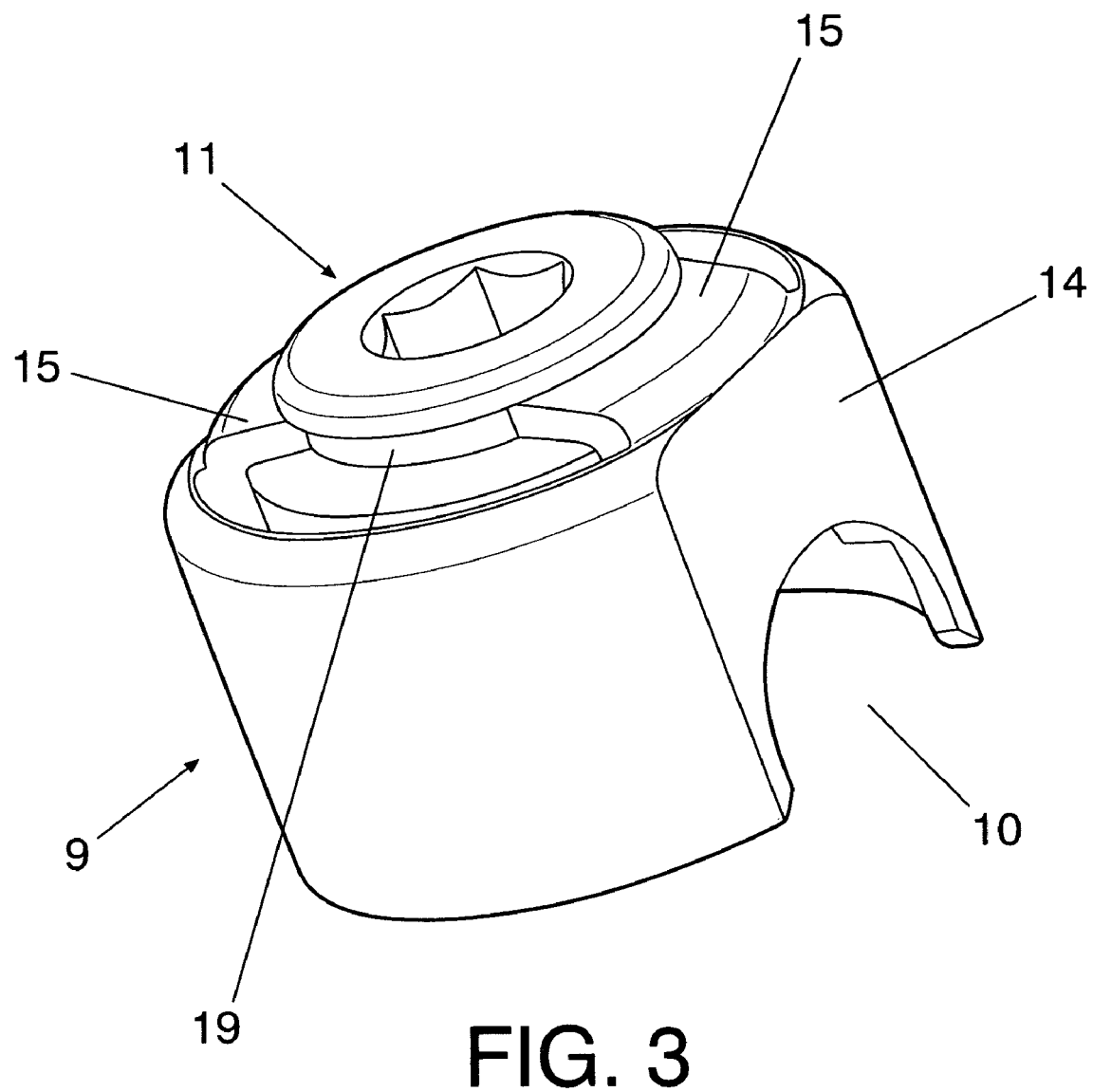
FIG. 3.—Depicts a perspective view of the closing screw linked to the locking cap.
Figure 5:
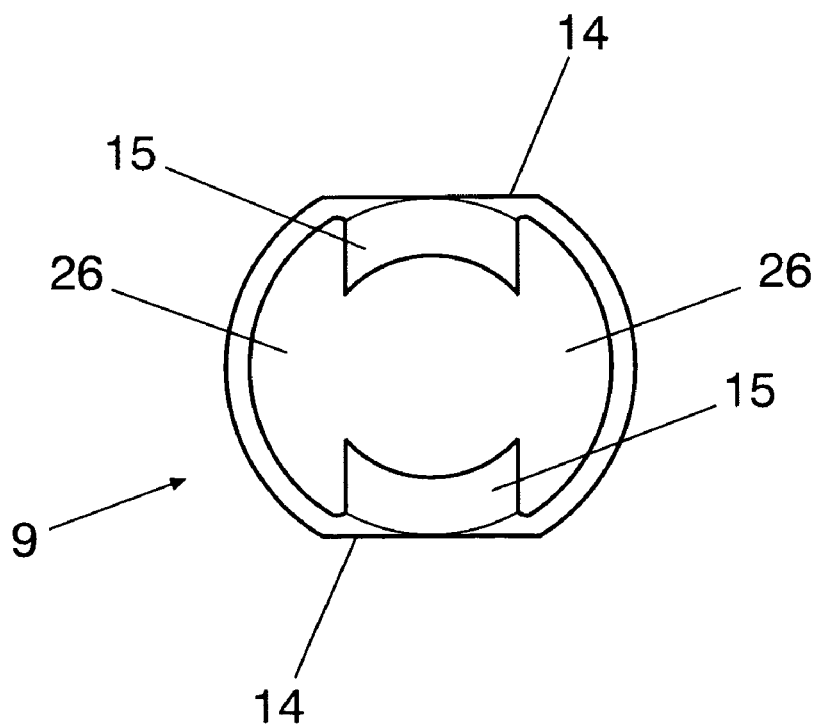
FIG. 5.—Depicts a plan view of the locking cap.

In FIGS. 5 and 6, it is also possible to see a couple of fins (15) that are diametrically opposed to each other and also depicted in FIG. 1, ending in a circular shape and leaning outwards, which come out over the top of the locking cap (9) and embrace an indentation (19) defined on the closing screw (11), as may be seen in FIG. 3, linking both parts in their axial movement and allowing the closing screw (11) to turn in terms of the locking cap (9).

FIG. 5 shows that between the two fins (15) and the wall of the locking cap (9), there are openings (26) that facilitate the passage of the tulip (6), which comes out on the top, while the fins (15) slide on the inside of the lateral notches (7) of the tulip (6).

Figure 7:
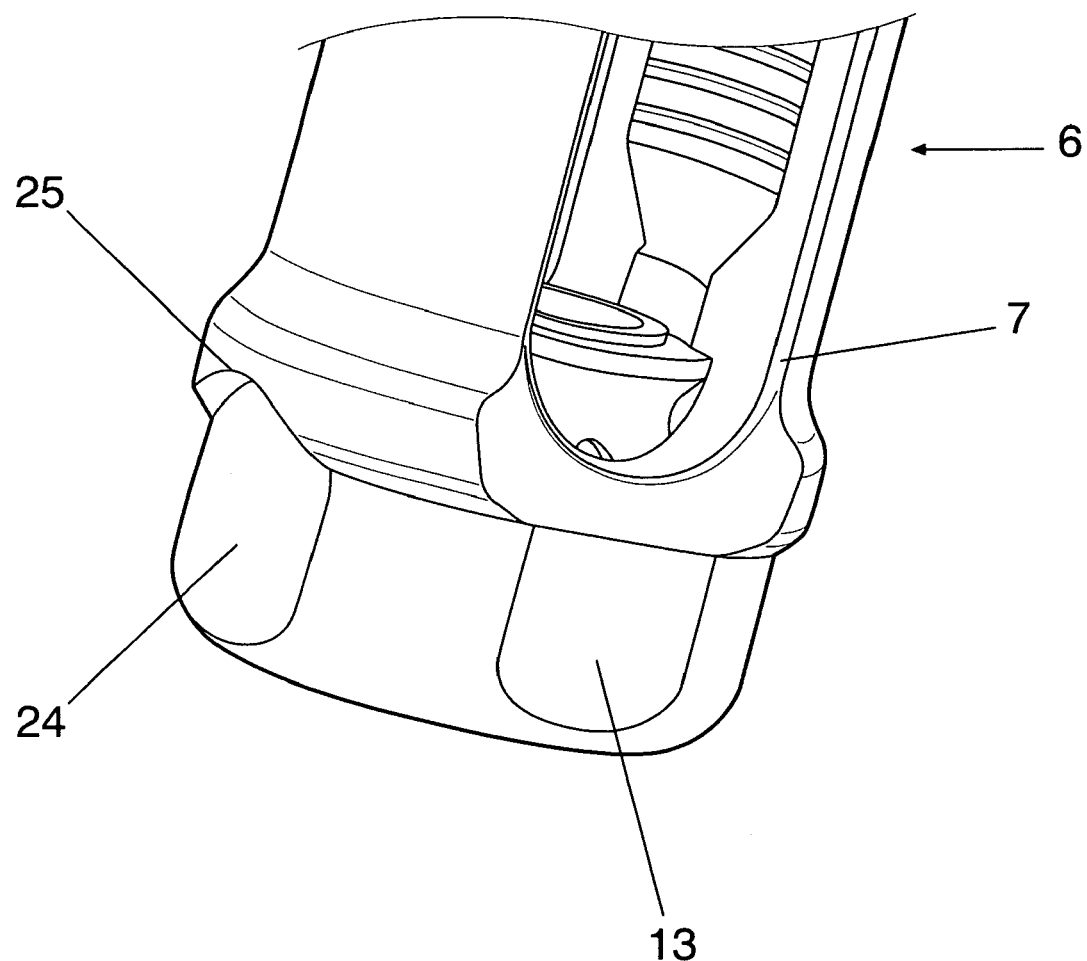
FIG. 7.—Depicts a partial perspective view of the tulip in which the flat indentations of same are represented.

FIG. 7 shows that the outer face of the tulip (6) shows an essentially circular general configuration that is interrupted by flat indentations (13) facing each other, located on the side in which the lateral notches (7) of the tulip (6) are located.

Moreover, FIGS. 3 and 4 show that the outer face of the locking cap (9) also presents an essentially circular general configuration, interrupted by opposite-facing flat indentations (14), on the outer face, in correspondence with the place in which the internal protuberances (12) are to be found.

These flat indentations (13, 14) on the tulip (6) and the locking cap (9) contribute to reduce the width of the device in the axial direction of the bar (8), preventing it from contacting another nearby device located on the same bar (8).

FIG. 7 also depicts further flat indentations (24) perpendicular to the first flat indentations (13) defined on the outer face of the body of the tulip (6), limited by a circular step (25) that facilitates the gripping of the ends of the assembly tool (100), as we shall describe later on.

Figure 8:
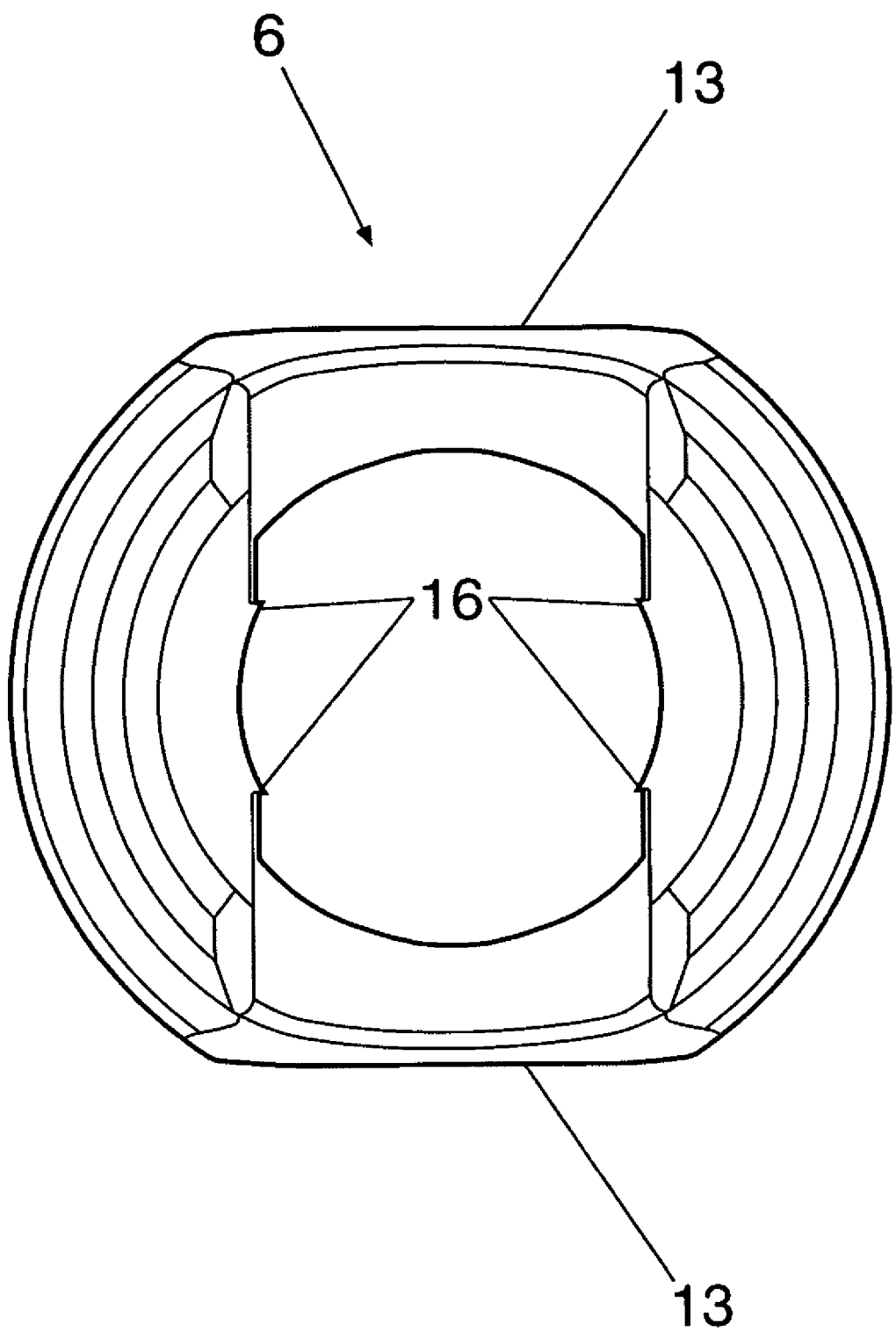
FIG. 8.—Depicts a plan view of the tulip.
Figure 9:
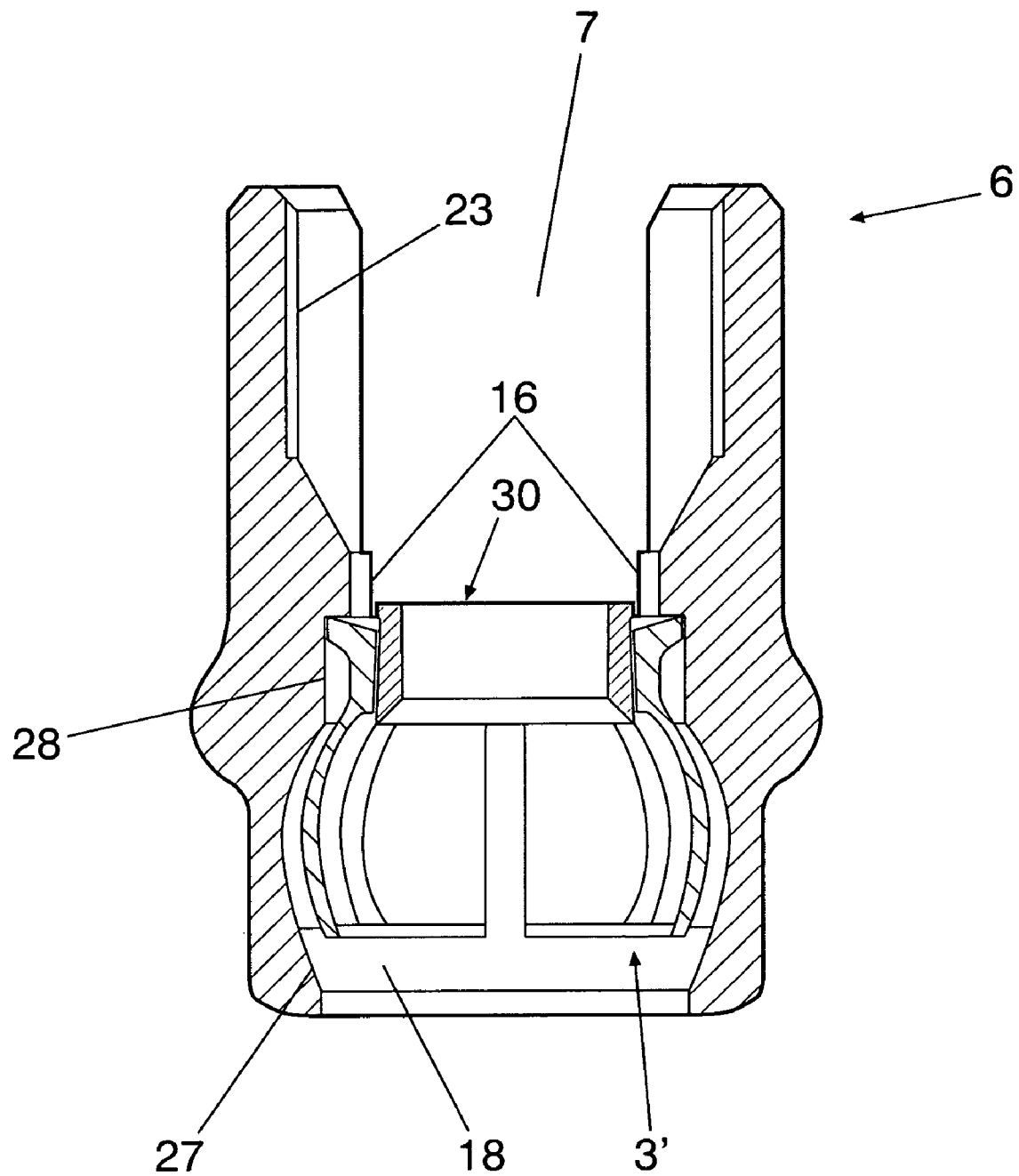
FIG. 9.—Depicts a sectioned view of the tulip with a type of rosette located inside.

On the other hand, FIGS. 1 and 2, for example, show that the tulip (6) has teeth on the inside (16), facing each other and also represented in FIGS. 8 and 9, which penetrate slightly into the space of the lateral notches (7), between which the bar (8) is held, thus increasing the bar's (8) resistance to sliding.

FIG. 1 also depicts that between these inner teeth (16) and the threaded sector (23) of the tulip (6), there is a conical sector (17) that establishes continuity between both surfaces and lends greater strength to the tulip (6), reducing its tendency to open when the closing screw penetrates (11).

Moreover, as may be seen in FIG. 9, the tulip (6) has a lower conical wall (27) in its lower cavity (18), which shall be described later on. On the other hand, the lower cavity (18) of the tulip (6) extends at the top in a cylindrical cavity (28) where it moves, guiding the upper promontory (4) of the rosette (3-3'), without losing the axial alignment between both.

Figure 11:
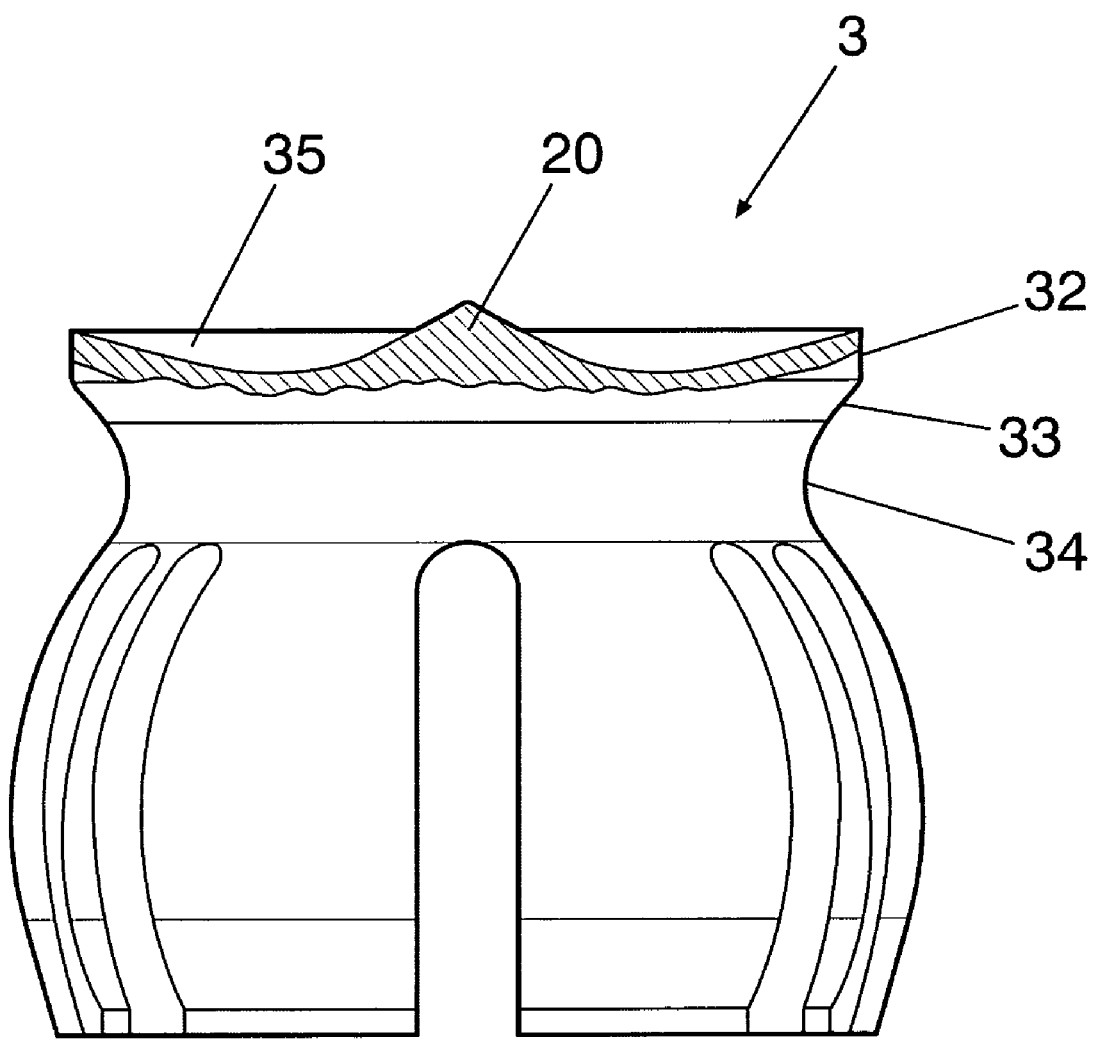
FIG. 11.—Depicts a view of another embodiment of rosette with a cut showing the inside shape of the upper promontory.

In one possible embodiment of the rosette (3-3"), represented in FIG. 1 or 11 for example, it has a rough flange (20) on the upper face of the promontory (4), which vertex constitutes the point of contact between the bar (8) and the rosette (3-3"). The pressure exerted by the closing screw (11) on the bar (8) is in turn transmitted from the bar (8) to the rosette (3-3") through this contact point on a uniform basis, as may be seen in FIG. 2, which means that the flexible slats (5) incide on the lower conical wall (27) of the tulip (6) and that the flexible slats (5) close on and embrace the head (2) of the pedicle screw (1).

In general terms, the rosette (3-3') allows for multiple orientation of the pedicle screw (1), in which case the rosette (3-3') is polyaxial. Another possibility has been provided for, as may be seen in FIG. 1, in which the rosette (3) incorporates a central internal protuberance (21) that fits on a cavity (22) defined on the head (2) of the pedicle screw (1) to establish a perpendicular position of the pedicle screw (1) as regards the rosette (3"), in which case the rosette is monoaxial (3").

Figure 10:
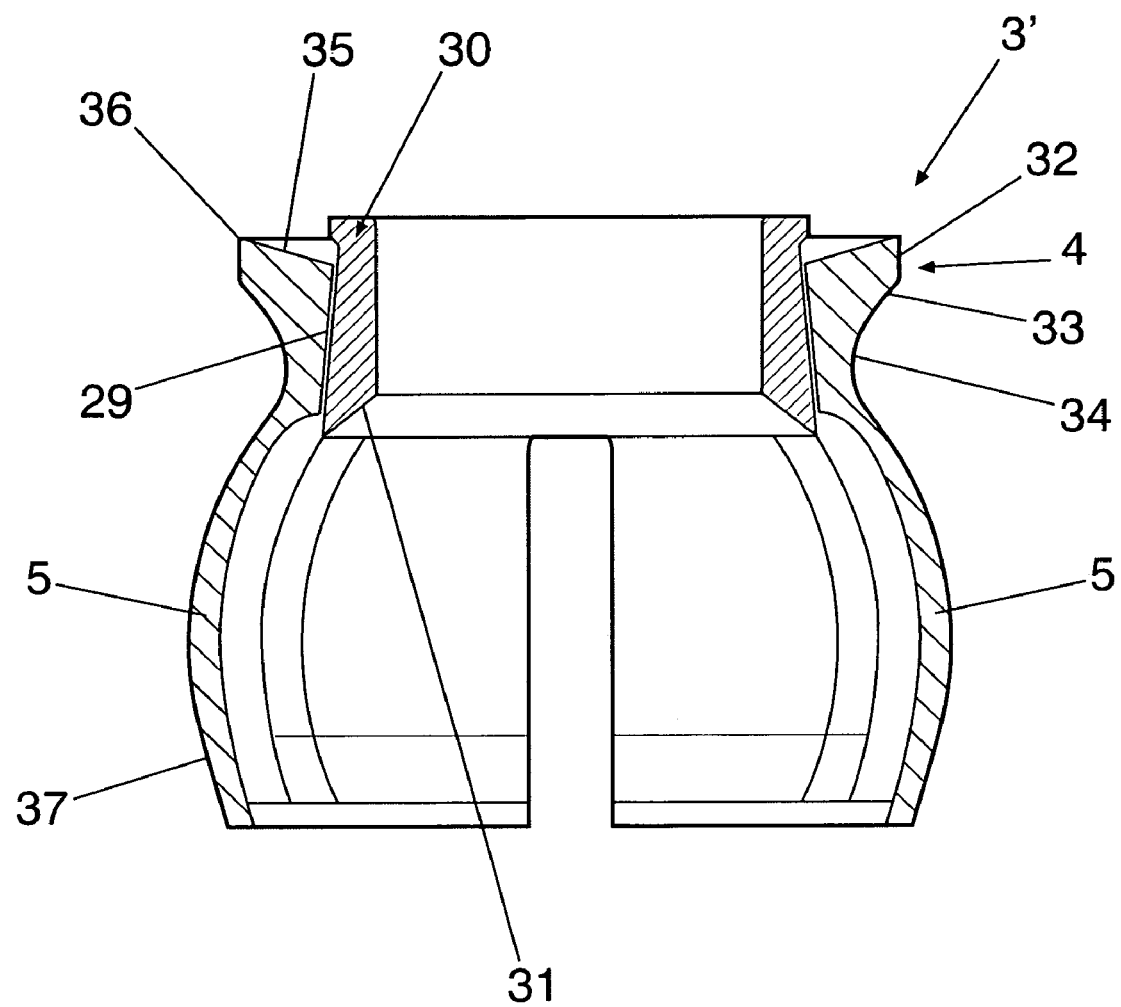
FIG. 10.—Depicts a sectioned view of the rosette in the previous figure.

In another embodiment of the rosette (3') represented in FIGS. 9 and 10, the rosette (3') has a wide opening (29) on the upper promontory (4), instead of the rough flange (20), in which a bushing (30) is housed with the possibility of axial movement by the pressure that the bar (8) exerts on the rosette (3'), which in turn exerts pressure on the head (2) of the pedicle screw (1), collaborating to strangle the head (2), and thus fixing the position of the pedicle screw (1).

The bushing (30), as represented in FIGS. 9 and 10, moves axially due to the pressure of the bar (8) and has a bevel (31) at the base of the wall that makes it up and which constitutes the contact surface on the head (2) of the pedicle screw (1).

In both embodiments of the rosette (3-3'), the upper promontory (4) of the rosette (3-3') has a cylindrical upper section (32) that allows for its guided movement in the cylindrical cavity (28) of the tulip (6), then a conical section (33), followed by a curvaceous-concave entrance (34) that allows to introduce the pincers that are used to remove the rosette (3-3') from the pedicle screw (1).

Also, in both cases, the rosette (3-3') has a conical indentation (35) on the upper face of the upper promontory (4), which is prolonged on the inside from a perimetrical edge (36), in the case of the first embodiment, it its prolonged with continuity on the rough flange (20) described previously, and in the case of the second embodiment, the conical indentation (35) ends at the opening (29).

Moreover, the rosette (3-3') incorporates its flexible slats (5) with a generally spherical shape, at the base of which there is a conical section (37) that adapts to the lower conical wall (27) of the tulip (6), to strangle the head (2) of the pedicle screw (1) by the bar (8) exerting pressure on the rosette (3) when they are pushed by the closing screw (11).

It is also important to highlight the fact that the closing screw (11) incorporates at least one rough flange (38), or projections or knurled or irregular surfaces, as may be seen in FIG. 1, which facilitate embedding and pushing on the bar (8).

Figure 12:
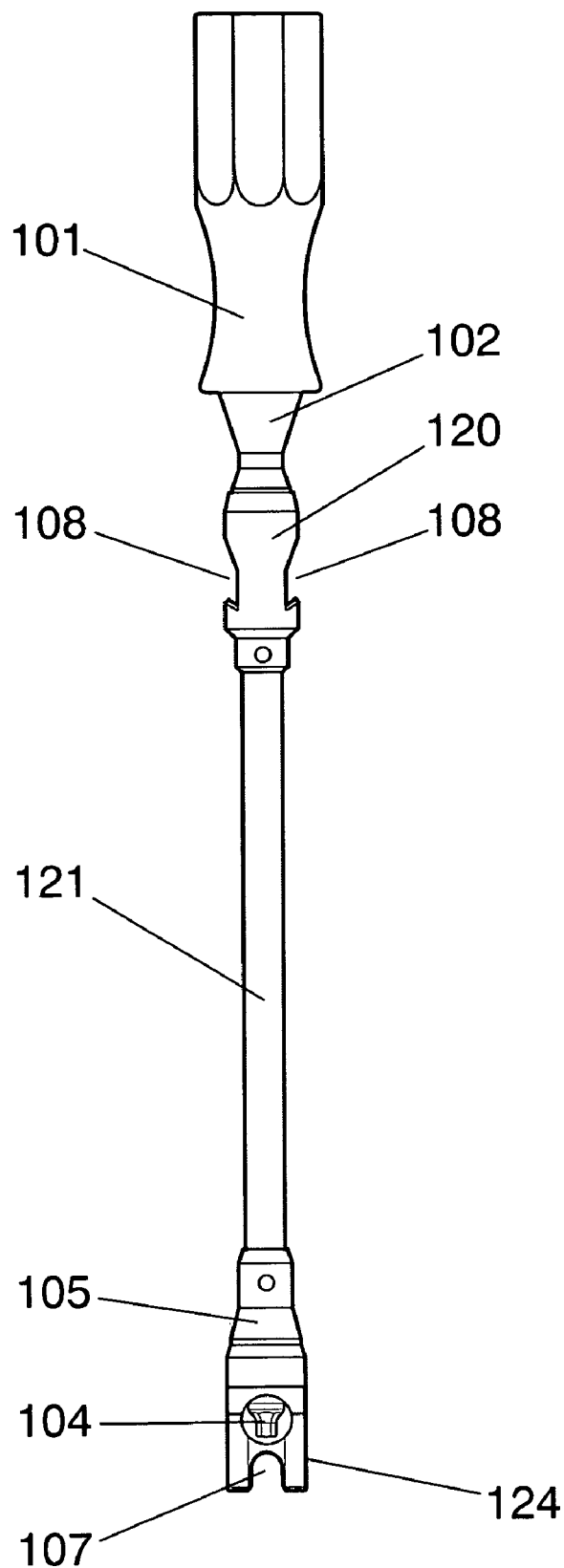
FIG. 12.—Depicts an elevation view of the tool without the lever.
Figure 13:
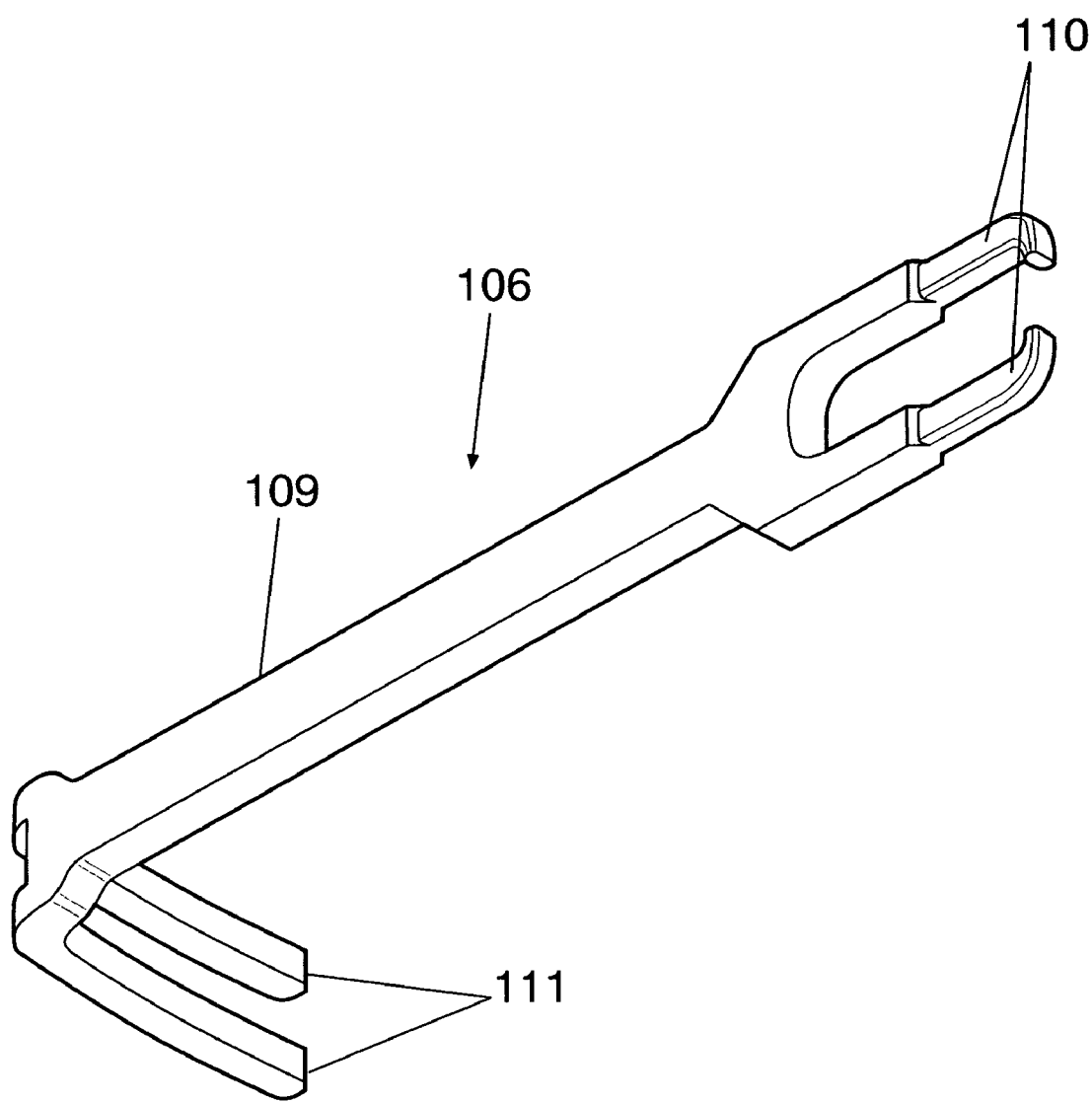
FIG. 13.—Depicts a perspective view of the lever.
Figure 15:
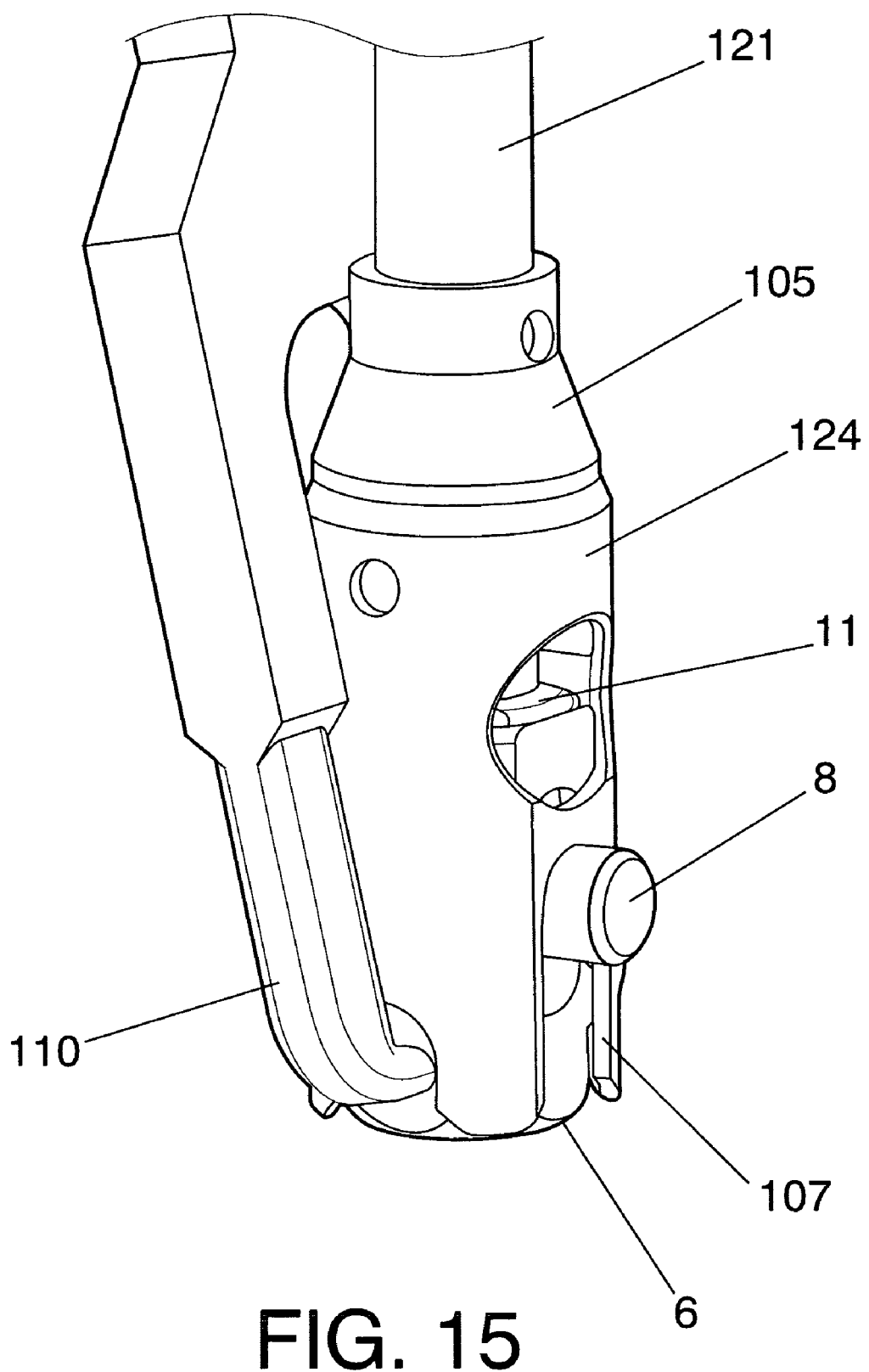
FIG. 15.—Depicts a perspective view of a detail of FIG. 14 that shows the attachment of the vase or sleeve and of the fork of the larger arm of the lever on the device.

The tool (100) used to assemble the fixation device described above is comprised of the following parts, as may be seen in FIG. 12:

a screwdriver equipped with:

a handle (101), a base (102) that is attached to the handle (101), a rod (103) that is attached on one end to the base (102) and which finalises on its other end in a connector (104), preferably hexagonal in shape and adaptable to the closing screw (11), a bushing (120), which may move longitudinally from the base (102) to cover or reveal a reference ring (123) that surrounds the aforementioned base (102), a tube (121) connected to the bushing (120) that surrounds the rod (103) almost entirely and around which the handle (101) with the base (102) and the rod (103) may turn, a centring support (105) that embraces and is connected to the tube (103) in the proximity of the connector (104), a sleeve (124) that is attached to the centring support (105), with lateral notches (107) that are destined to fit on the bar (8) of the fixation device, as may be seen in FIG. 15, and a lever (106) that is represented in FIG. 13.

The sleeve (124) depicts an inner diameter with clearance with the diameter of the locking cap (9) in order to guarantee alignment and the matching of the closing screw (11) with the threaded sector (23) of the tulip (6).

On the other hand, the bushing (120) has lateral indentations (108) facing each other.

It is important to highlight that the screwdriver constitutes a fixed block formed by bushing (120), tube (103), centring support (105), sleeve (124), in which the sleeve (124) attaches to the bar (8). In this position, when the handle (101) is turned, the base (102) turns and also the rod (103) that causes the connector (104) to turn either to screw or unscrew.

The connector (104) is hexagonal in shape with approximately 10° conicity, which allows it to attach and fit on the closing screw (11) and therefore bring the tool (100) with the closing screw (11) closer to the tulip (6).

Normally, once the pedicle screw (1) has been introduced, the rosette (3-3') and the tulip (6) are situated in a particular position. The bar (8) that comes from another fixation device may be situated in the notches (7) of the tulip (6) in a position in which the closing screw (11) attached to the screwdriver contacts the bar (8). The position of the bar (8) may be so high that it may not allow for free threading of the closing screw (11) on its first threads, creating the possibility that they may break and that the threading may be incorrect.

The lever (106) is used in order to bring down the bar (8) to freely commence threading the closing screw (11). It is necessary to use the lever (106) when the reference ring (123) is not visible. This indicates that the positioning of the closing screw (11) does not rest on the tulip, as the sleeve (124), and its notch (107), is seated on the bar (8) and the latter is not in its corresponding position on the rosette (3'), but in a much higher position.

Figure 14:
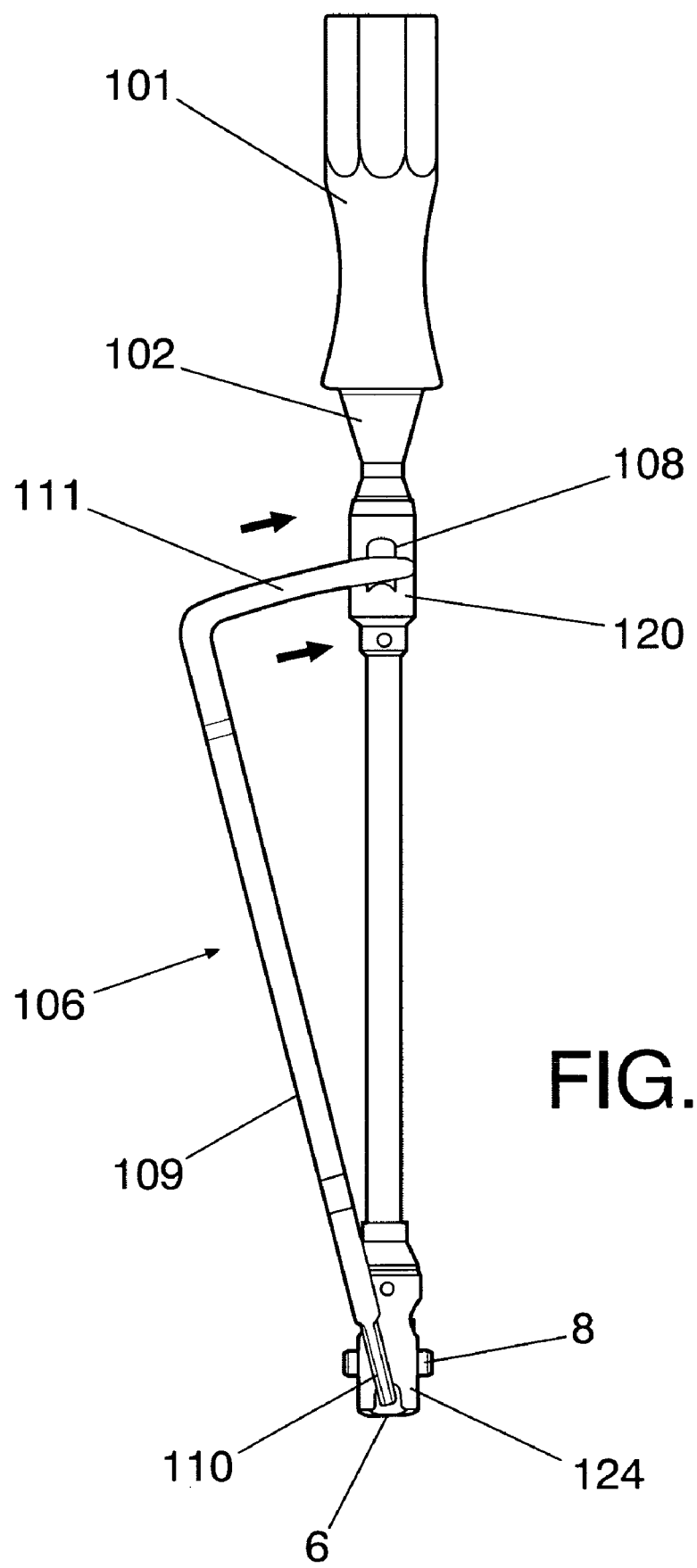
FIG. 14.—Depicts a lateral view of the tool attached to the fixation device in the initial position, before carrying out the pivoting movement of the lever.
Figure 16:
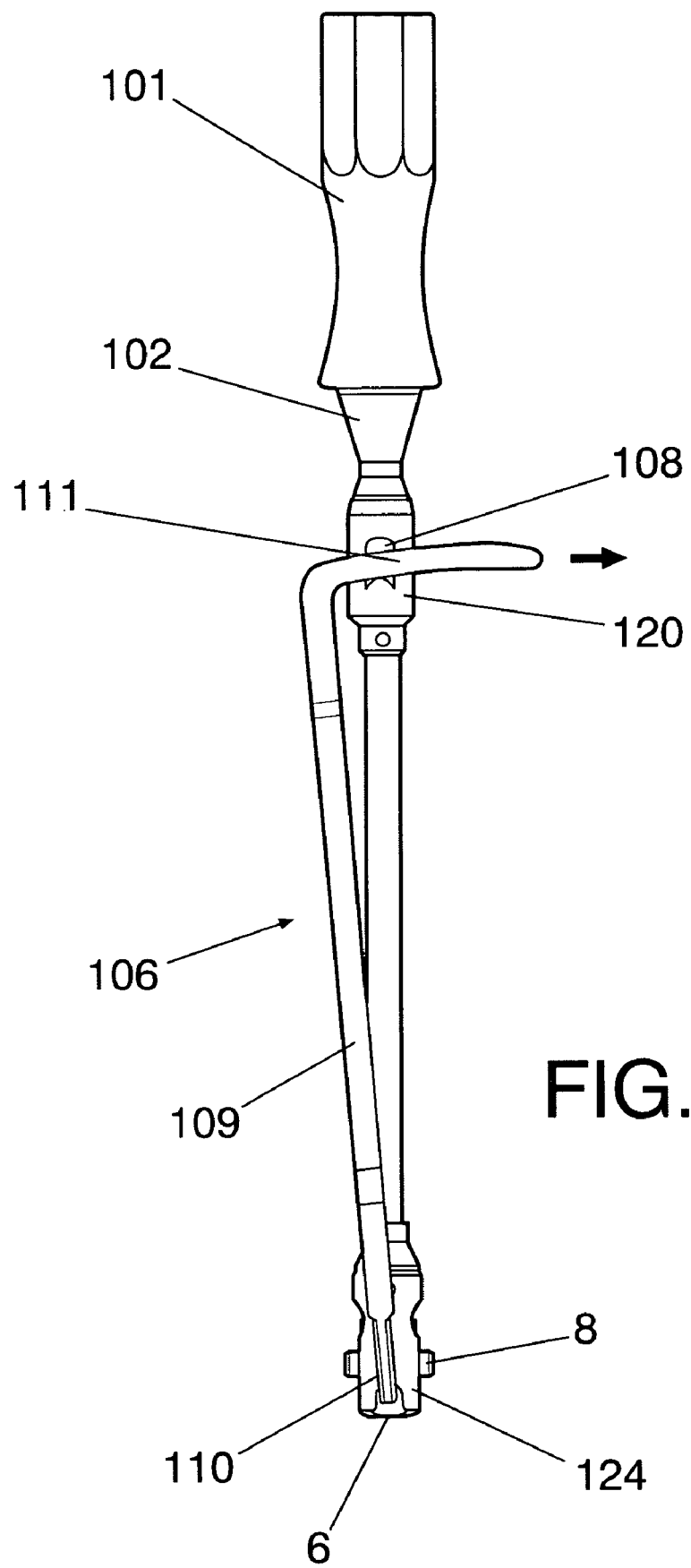
FIG. 16.—Depicts a perspective view of the tool attached to the fixation device in the final position, after the lever has been turned, bringing the tulip close to the closing screw.
Figure 17:
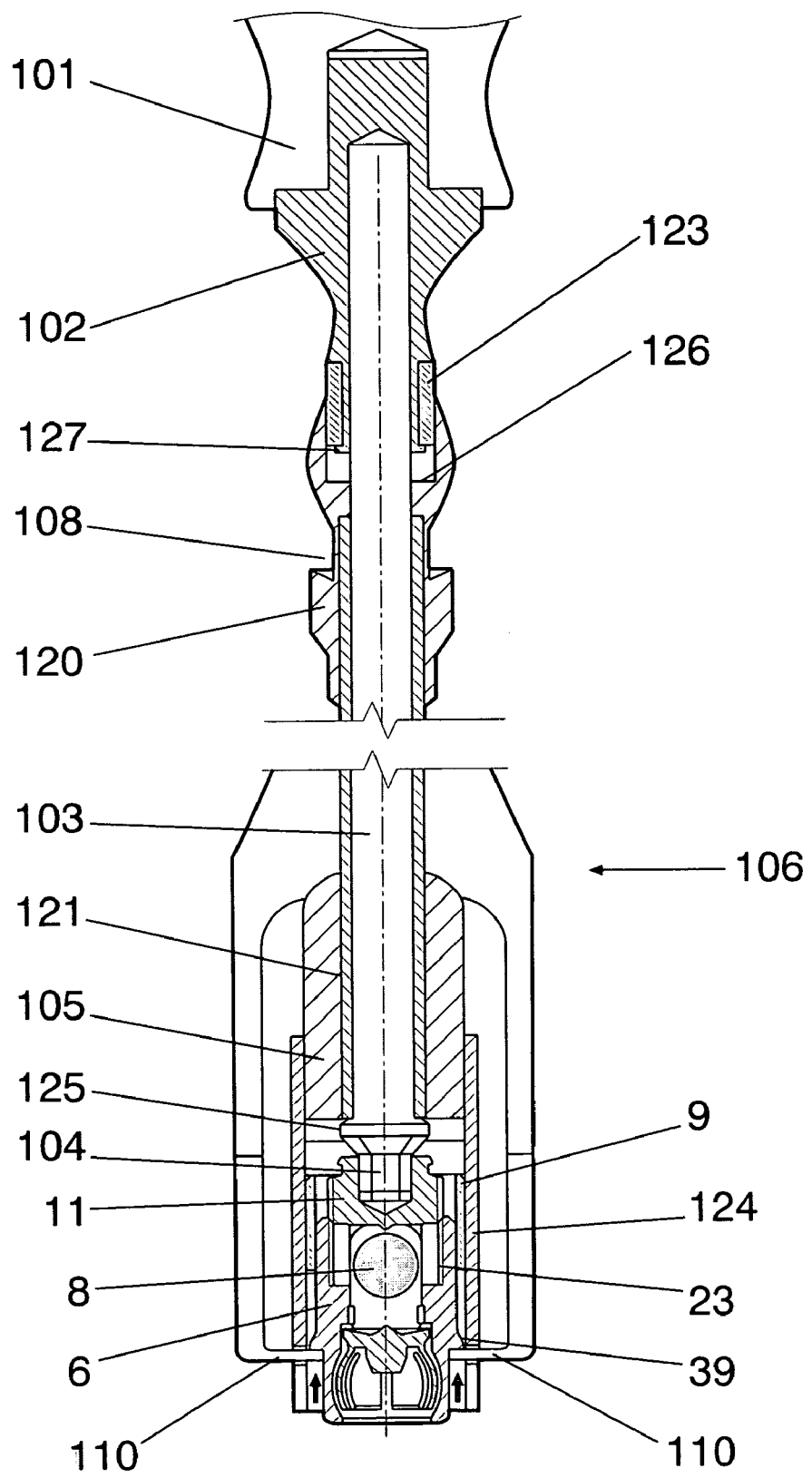
FIG. 17.—Depicts a sectioned view of the tool, attached to the fixation device with the bushing, showing how the lever has pushed the tulip as far as the closing screw.

As may be seen in FIG. 13, the lever (106) is in the shape of an L and is formed by a larger arm (109) ending in a fork (110), the ends of which adapt to the second indentations (24) of the tulip (6), meeting the step (25) on which the lever pivots (106), as may be seen in FIG. 15, and by a smaller arm (111) in the form of a fork which wings slide through the lateral indentations (108) of the base of the bushing (120) in a pivoting movement of the lever (106), as may be seen in FIGS. 14 and 16, thus pushing the ends of the fork (110) of the larger arm (109) on the tulip (6) in an axial direction towards the closing screw (11) in order to facilitate fitting the latter on the tulip (6) and then proceed to threading.

On the other hand, once the closing screw (11) has been fully threaded on the tulip (6), the screwdriver will be extracted.

In order to facilitate this operation, the end of the course of the rod (103) and the limit of the notch (107) of the sleeve (124) that rests on the bar (8) mean that the rod (104) of the screwdriver cannot descend any further, while the closing screw (11) advances as it is threaded, thus separating the rod (104) and the closing screw (11), and thus freeing the instrument to be effortlessly extracted.

Moreover, it is also important to note that there is a projection (125) between the connector (104) and the rod, which prevents the tube from coming out (121).

Figure 18:
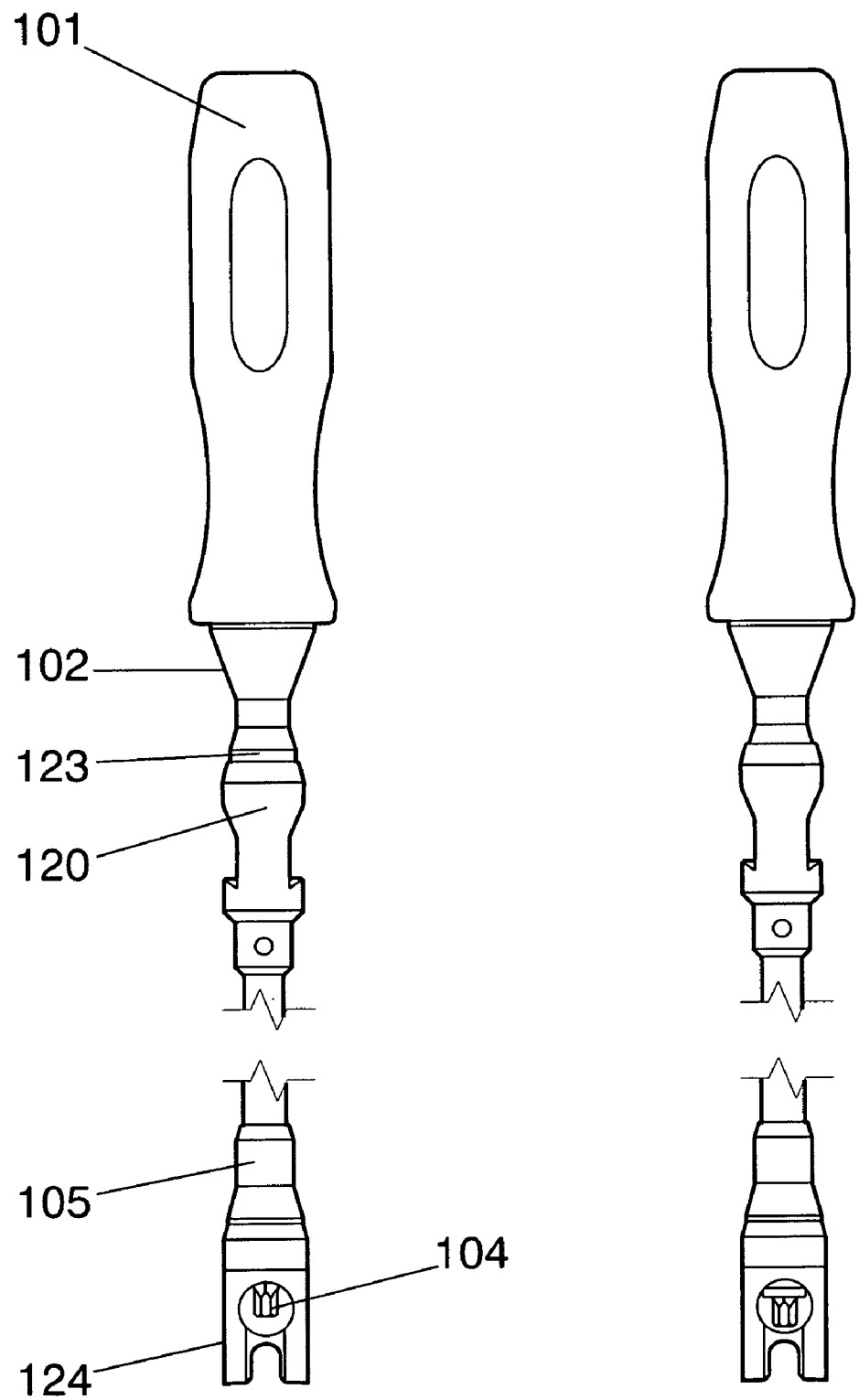
FIG. 18.—Depicts a lateral view of the screw driver in which two positions may be observed, one corresponding to the situation in which the hexagonal connector would be on the closing screw and the other in the situation where the screwdriver has been separated.
Figure 20:
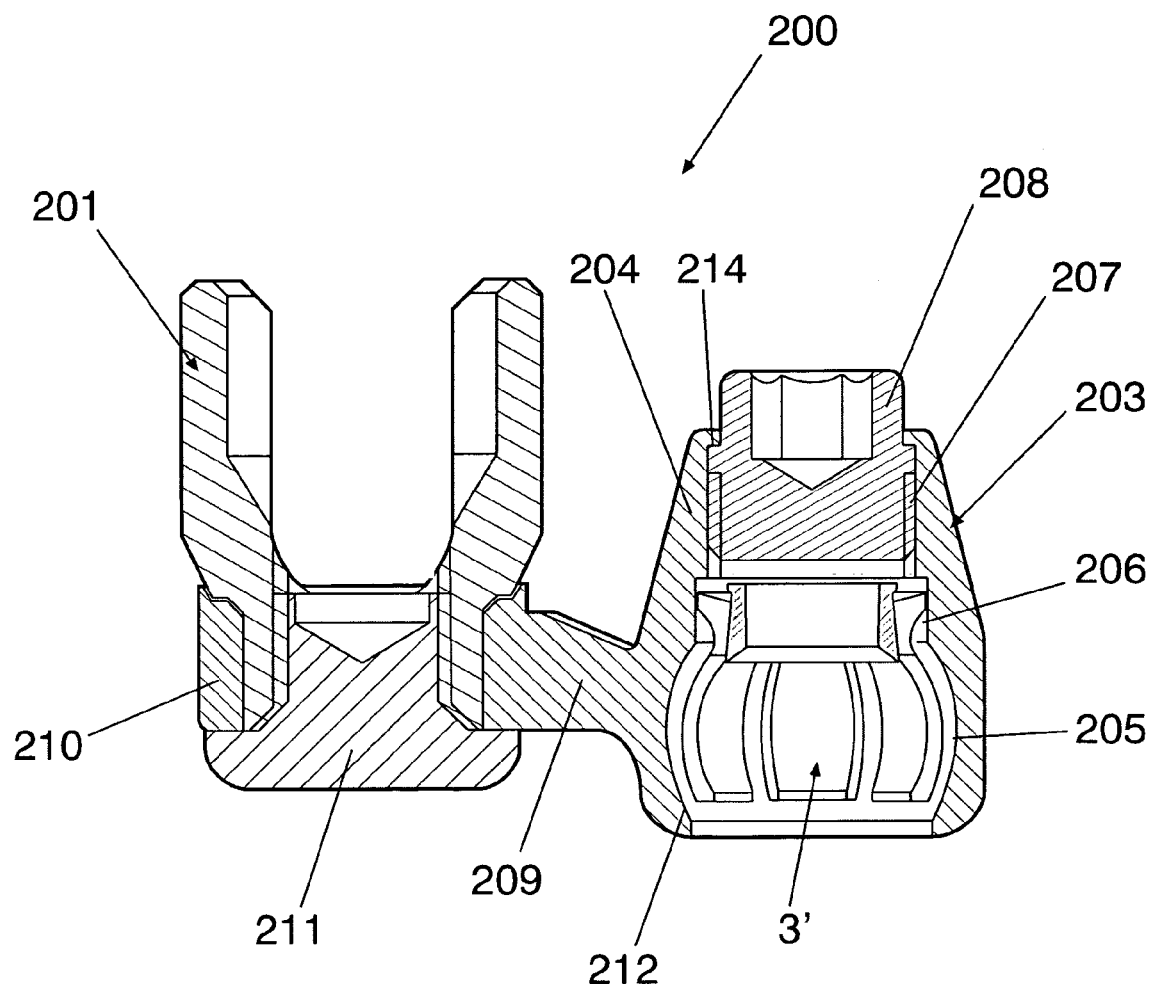
FIG. 20.—Depicts a view that is similar to the previous figure, in which the lateral body houses another type of rosette.
Figure 21:
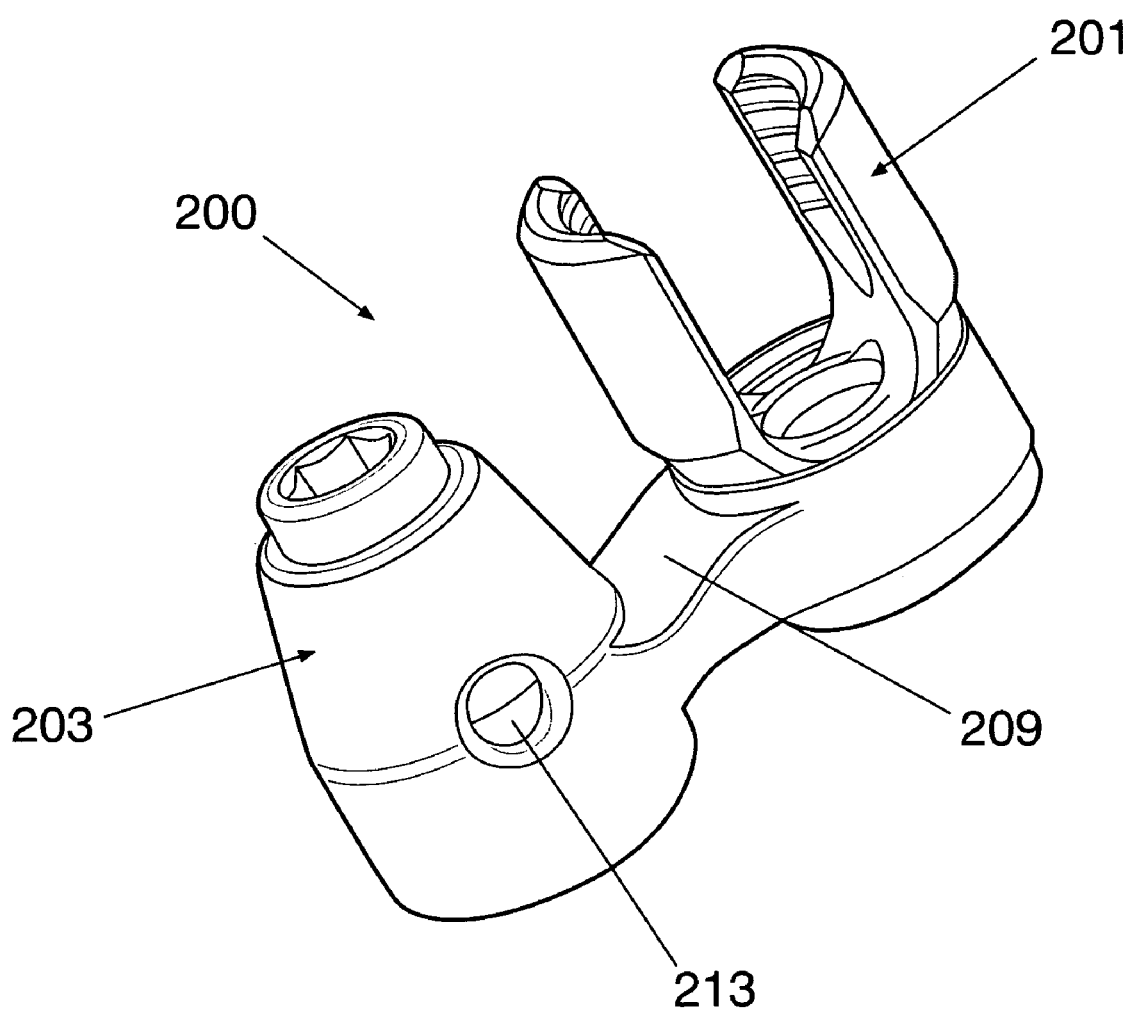
FIG. 21.—Depicts a perspective view of the lateral connector.

In FIGS. 18 and 20, another type of vertebral fixation device has been represented, consisting of a lateral connector (200) used to correct the lateral deviation of the vertebrates from the vertical position of the spine.

This device is linked to the joining bar (8) to which at least one other device of the type described previously, or another lateral connector (200), is attached.

Figure 19:
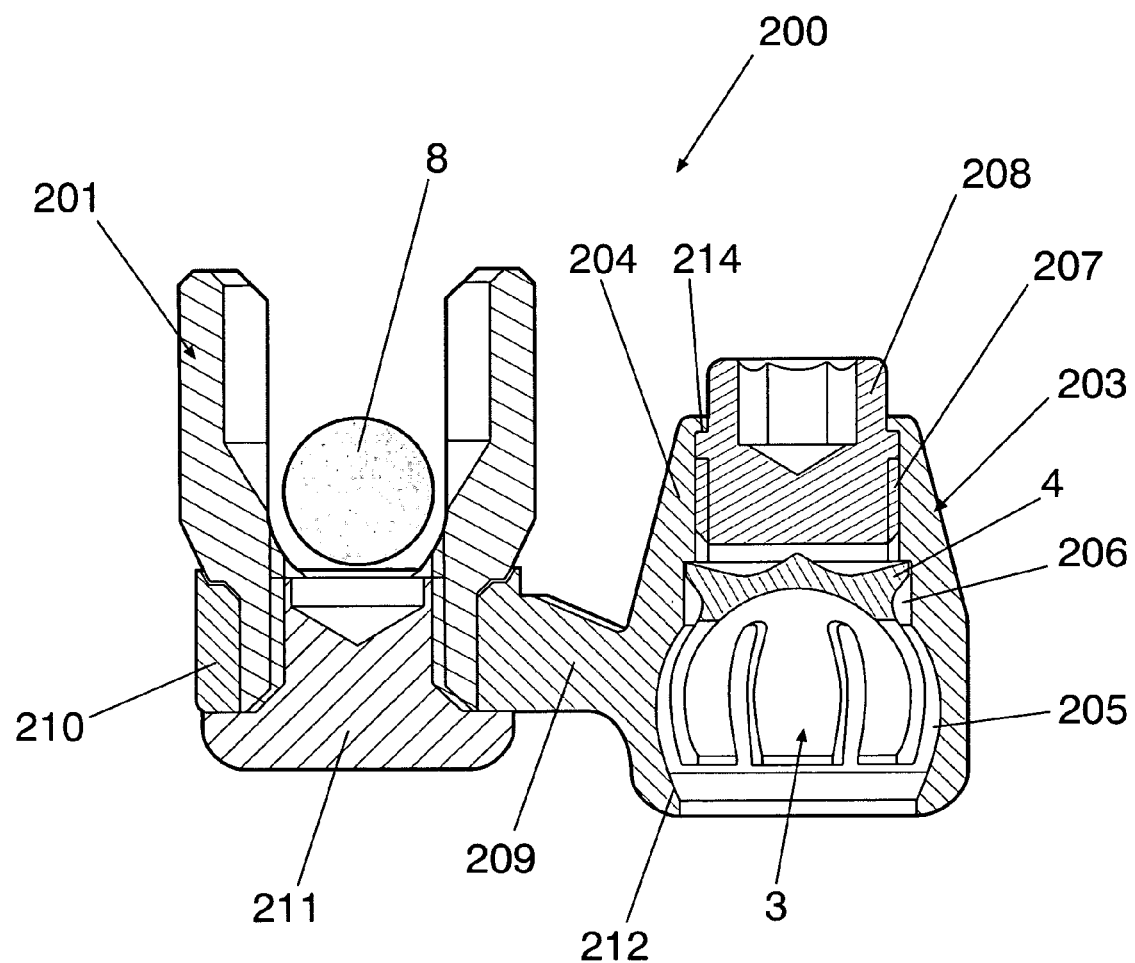
FIG. 19.—Depicts a sectioned view of the lateral connector in which a type of rosette is located.

In FIGS. 18 to 20, the lateral connector (200) is seen to be formed by an auxiliary tulip (201), with notches (202) through which the bar (8) is introduced, to which the auxiliary tulip (201) is fixed by means of the corresponding joining means, such as the closing screw (11) and the locking cap (9) described previously, and around which a rosette-carrier (203) that houses the pedicle screw (1) attached by means of a rosette (3-3') rotates with the capacity for 360° free rotation around the longitudinal axis of the auxiliary tulip (201).

The rosette-carrier (203) constitutes a body (204) with a lower cavity (205) and a middle cavity (206) that contain the rosette (3-3') and a threaded upper cavity (207) containing a tightening screw (208) that moves, inciding on the rosette (3-3') to embrace the head (2) of the pedicle screw (1), as well as an arm (209) that extends sideways from the body (204) and ends in a bushing (210) that embraces the auxiliary tulip (201) on a rotating basis.

Below the auxiliary tulip (201), there is a lid (211) which is threaded on same, fixing the position of the arm (209) and therefore of the rosette-carrier (203) as regards the auxiliary tulip (201). This situation also defines the relative position of the pedicle screw (1) in terms of the bar (8) to which the auxiliary tulip (201) has been fixed in advance.

The lower cavity (205) of the rosette-carrier (203) is spherical in shape and ends in a conical sector (212) with which the slats of the rosette (3-3') contact in their movement by the action of the tightening screw (208) that determines that the slats should embrace the head (2) of the pedicle screw (1).

On the other hand, the middle cavity (206) is cylindrical in shape and the promontory (4) of the rosette (3-3') is guided along it.

FIGS. 18 and 19 show that the body (204) of the rosette-carrier (203) incorporates stops (213) in the threaded upper cavity (207), which prevent the tightening screw (208) from coming out at the top.

Moreover, the body (204) has transversal holes (213) at the height of the threaded upper cavity (207), represented in FIG. 20, through which it is possible to introduce a tool to remove the rosette (3-3'-3") of the pedicle screw (1).

FIG. 18 depicts a type of rosette (3), whereas FIG. 19 depicts another type of rosette (3') with bushing (30). In any case, they are polyaxial rosettes (3-3') that allow to move the pedicle screw (1) in any direction. FIG. 1 depicts the monoaxial rosette (3") that allows only one orientation of the pedicle screw (1).

The invention claimed is:

1. Vertebral fixation device comprised of the following:
   a pedicle screw, which constitutes a head with a partially spherical configuration, intended for introduction in a vertebra;
   a rosette with an upper promontory from which flexible slats come down, intended to press on the head, fixing the pedicle screw and placing the device at a desired angle;
   a tulip with two lateral notches, a threaded inner sector, and partially spherical lower cavity, ending in a lower conical wall, in which the rosette is housed;
   a bar, which constitutes a link with other devices, housed in the lateral notches;
   a locking cap with circular openings to allow the bar to pass through, which moves axially on an outer face of the tulip, and
   a closing screw associated to the locking cap which is threaded on the threaded sector inside the tulip and fixes the bar against the rosette;
   wherein the tulip and the locking cap comprise opposite-facing flat indentations on an outer face of the tulip and the locking cap, respectively;
   wherein the rosette is configured to receive pressure directly from the bar in the absence of a complementary tightening screw to fix the rosette to the head of the pedicle screw; and
   wherein the rosette has a conical indentation on an upper face of the upper promontory, which is prolonged towards an inside from a perimeter edge, the flexible slats of the rosette incorporate a conical section that adapts to the lower conical wall of the tulip, to strangle the head of the pedicle screw when the bar exerts pressure on the rosette when both are pushed by the closing screw; and
   wherein the rosette has a wide opening that is prolonged in a center of the rosette after the conical indentation in which a bushing is housed with a possibility of axial movement by the pressure that the bar exerts on the rosette, which in turn exerts pressure on the head of the pedicle screw collaborating to strangle the head and thus fixing the position of the pedicle screw.

2. Vertebral fixation device, according to claim 1, wherein the rosette has a cylindrical upper section on its lateral face, then a conical section and then a curvaceous-concave entrance that allows to introduce pincers to remove the rosette from the pedicle screw.

3. Vertebral fixation device, according to claim 1, wherein the rosette incorporates a central internal protuberance which fits on a cavity defined on the head of the pedicle screw to establish a perpendicular position of the pedicle screw as regards the rosette.

4. Vertebral fixation device, according to claim 1, wherein the tulip has a lower cavity of an upper cylindrical section in which the upper cylindrical section of the rosette has a guided movement.

5. Vertebral fixation device, according to claim 1,
   wherein the locking cap incorporates protuberances defined on an inner face of the locking cap that are situated in an opposite-facing configuration as a continuation of the circular openings, of a width that is slightly less than a width of the lateral notches of the tulip, on which it fits, guiding the locking cap in an axial direction and facilitating the positioning of the closing screw and its threading on the threaded sector of the tulip while also moving and adjusting the bar against the rosette.

6. Vertebral fixation device, according to claim 5, wherein the outer face of the locking cap presents an essentially circular general configuration interrupted by opposite-facing flat indentations, located on a side on which the circular openings of the locking cap are located, which reduce a width of device in an axial direction of the bar, avoiding contact with another nearby device situated on the same bar.

7. Vertebral fixation device, according to claim 5, wherein the opposite-facing internal protuberances are circular in shape in order to house the closing screw with clearance, ensuring an alignment of the closing screw and the tulip when threading commences.

8. Vertebral fixation device, according to claim 5, wherein the locking cap incorporates diametrically opposed fins that are finished in a circular shape and leaning forwards, coming out over a top of the locking cap and embracing an indentation defined in the closing screw; linking the locking cap and the closing screw in an axial movement and allowing to turn the closing screw in terms of the locking cap.

9. Vertebral fixation device, according to claim 5, wherein there are openings between two fins and a wall of the locking cap, which facilitate a passage of the tulip that comes out at a top of the locking cap, while the fins slide on an inside of the lateral notches of the tulip.

10. Vertebral fixation device, according to claim 5, wherein the tulip has a cylindrical upper cavity above the lower cavity, in which a cylindrical upper section is guided, defined on the promontory of the rosette during a movement of the bar against the rosette.

11. Vertebral fixation device, according to claim 5, wherein the rosette has a rough flange that is prolonged in a center of the rosette after the conical indentation, which vertex constitutes the contact point between the bar and the rosette.

12. Vertebral fixation device, according to claim 5, wherein the outer face of the tulip, presents an essentially circular general configuration that is interrupted by the first opposite-facing flat indentations, located on a side on which the lateral notches of the tulip are located, which reduce a width of the device in an axial direction of the bar, avoiding contact with another nearby device located on the same bar.

13. Vertebral fixation device, according to claim 5, wherein the outer face of the tulip presents the flat indentations that are perpendicular to a first flat indentations limited by a circular step.

14. Vertebral fixation device, according to claim 5, wherein the tulip has opposite-facing lower teeth that penetrate slightly into a space of the lateral notches, between which they grip the bar, increasing resistance of the bar to sliding.

15. Vertebral fixation device, according to claim 14, wherein there is a conical sector between the lower teeth and the inner threaded sector of the tulip, which establishes a continuity between both surfaces of the lower teeth and the inner threaded sector and lends strength to the tulip, thus reducing a tendency to open when the closing screw penetrates.

16. Vertebral fixation device, according to claim 5, wherein the tulip incorporates on its outer face a perimetrical projection with the same diameter as the locking cap.

* * * * *